(12) United States Patent
Klingemann et al.

(10) Patent No.: US 12,378,300 B2
(45) Date of Patent: Aug. 5, 2025

(54) ELIMINATION OF CD19-POSITIVE LYMPHOID MALIGNANCIES BY CD19-CAR EXPRESSING NK CELLS

(71) Applicant: ImmunityBio, Inc., San Diego, CA (US)

(72) Inventors: Hans G. Klingemann, San Diego, CA (US); Laurent H. Boissel, San Diego, CA (US); Patrick Soon-Shiong, San Diego, CA (US)

(73) Assignee: ImmunityBio, Inc., San Diego, CA (US)

( * ) Notice: Subject to any disclaimer, the term of this patent is extended or adjusted under 35 U.S.C. 154(b) by 1160 days.

(21) Appl. No.: 16/934,606

(22) Filed: Jul. 21, 2020

(65) Prior Publication Data
US 2020/0376033 A1    Dec. 3, 2020

Related U.S. Application Data

(62) Division of application No. 16/529,251, filed on Aug. 1, 2019, now Pat. No. 10,765,701.

(60) Provisional application No. 62/753,719, filed on Oct. 31, 2018.

(51) Int. Cl.
| | | |
|---|---|---|
| C07K 14/735 | (2006.01) | |
| A61K 9/00 | (2006.01) | |
| A61K 40/15 | (2025.01) | |
| A61K 40/31 | (2025.01) | |
| A61K 40/42 | (2025.01) | |
| A61P 35/00 | (2006.01) | |
| A61P 35/04 | (2006.01) | |
| C07K 14/54 | (2006.01) | |
| C07K 14/55 | (2006.01) | |
| C07K 14/725 | (2006.01) | |
| C07K 16/28 | (2006.01) | |
| C12N 5/0783 | (2010.01) | |
| A61K 38/00 | (2006.01) | |
| A61K 39/00 | (2006.01) | |

(52) U.S. Cl.
CPC ...... *C07K 14/70535* (2013.01); *A61K 9/0019* (2013.01); *A61K 40/15* (2025.01); *A61K 40/31* (2025.01); *A61K 40/4211* (2025.01); *A61P 35/00* (2018.01); *A61P 35/04* (2018.01); *C07K 14/5443* (2013.01); *C07K 14/55* (2013.01); *C07K 14/7051* (2013.01); *C07K 16/2803* (2013.01); *C12N 5/0646* (2013.01); *A61K 38/00* (2013.01); *A61K 2039/54* (2013.01); *A61K 2239/31* (2023.05); *A61K 2239/48* (2023.05); *C07K 2317/622* (2013.01); *C07K 2317/732* (2013.01); *C07K 2317/76* (2013.01); *C07K 2319/02* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | |
|---|---|---|
| 7,618,817 B2 | 11/2009 | Campell |
| 8,034,332 B2 | 10/2011 | Klingemann |
| 8,313,943 B2 | 11/2012 | Campell |
| 9,150,636 B2 | 10/2015 | Campell |
| 9,181,322 B2 | 11/2015 | Campell |
| 10,138,462 B2 | 11/2018 | Klingemann |
| 10,456,420 B2 | 10/2019 | Lee et al. |
| 10,738,279 B2 | 8/2020 | Lee |
| 11,077,143 B2 | 8/2021 | Klingemann et al. |
| 11,655,452 B2 | 5/2023 | Ma et al. |
| 2002/0068044 A1 | 6/2002 | Klingemann |
| 2018/0100016 A1 | 4/2018 | Song |
| 2018/0163176 A1 | 6/2018 | Lee |
| 2018/0187149 A1 | 7/2018 | Ma et al. |
| 2018/0193383 A1 | 7/2018 | Lee et al. |
| 2020/0129553 A1 | 4/2020 | Klingemann et al. |

FOREIGN PATENT DOCUMENTS

| | | |
|---|---|---|
| CN | 105384820 A | 3/2016 |
| CN | 107427578 A | 12/2017 |
| CN | 107709552 A | 2/2018 |
| CN | 108300698 A | 7/2018 |
| JP | 2018-510881 A | 4/2018 |
| KR | 10-2018-0008862 A | 1/2018 |
| WO | 98/49268 A1 | 11/1998 |
| WO | 2016/160602 A2 | 10/2016 |
| WO | 2016/201304 A1 | 12/2016 |
| WO | 2018/064594 A2 | 4/2018 |
| WO | 2018/098306 A1 | 5/2018 |
| WO | 2018/129346 A1 | 7/2018 |
| WO | 2018/165291 A1 | 9/2018 |
| WO | 2019/152513 A1 | 8/2019 |
| WO | 2019/226708 A4 | 12/2019 |
| WO | 2020/028654 A1 | 2/2020 |

(Continued)

OTHER PUBLICATIONS

Yu et al., Synthetic fusion protein design and applications Biotech. Adv., vol. 33, 155-164.*
Chen et al., Fusion protein linkers: Property, design and functionality, Advanced Drug Delivery Reviews 65 (2013) 1357-1369.*
Notice of Allowability for U.S. Appl. No. 17/341,098, filed Mar. 8, 2023; pp. 1-5.*
Decision of Refusal received for Japanese Patent Application Serial No. 2020-556293 dated Jul. 22, 2022, 4 pages. (Including English Translation).
Notice of Final Rejection received for Korean Patent Application Serial No. 10-2020-7028888 dated Jul. 14, 2023, 8 pages. (Including English Translation).

(Continued)

*Primary Examiner* — Michael D Burkhart
(74) *Attorney, Agent, or Firm* — Umberg Zipser LLP; Martin Fessenmaier; Priti Phukan

(57) ABSTRACT

Provided herein are compositions of NK-92® cells that express a CD19 CAR, CD16 and IL2, and the method of using these cells to and treat cancer in a patient.

19 Claims, 16 Drawing Sheets

Specification includes a Sequence Listing.

(56) References Cited

FOREIGN PATENT DOCUMENTS

| WO | 2020/028656 A1 | 2/2020 |
|---|---|---|
| WO | 2020/091869 A1 | 5/2020 |

OTHER PUBLICATIONS

Notice of Allowance received for Canadian Patent Application Serial No. 3,092,709 dated Jul. 4, 2023, 1 page.
Examination Report received for Australian Patent Application Serial No. 2019371340 dated Nov. 23, 2021, 3 pages.
Examination Report No. 2 received for Australian Patent Application Serial No. 2019371340 dated Jan. 14, 2022, 5 pages.
Notice of Acceptance received for Australian Patent Application Serial No. 2019371340 dated Feb. 18, 2022, 3 pages.
Extended European Search Report received for EP Patent Application Serial No. 19879733.4 dated Oct. 29, 2021, 8 pages.
International Search Report and Written Opinion received for PCT Application Serial No. PCT/US2019/044691, dated Nov. 15, 2019, 14 pages.
Liu et al., "Cord blood NK cells engineered to express IL-15 and a CD19-targeted CAR show long-term persistence and potent anti-tumor activity", Leukemia, Feb. 2018, vol. 32, No. 2, pp. 520-531.
Herberman et al., "Natural Killer Cells: Their Roles in Defenses Against Disease", Science, 1981, vol. 214, pp. 24-30.
Gong et al., "Characterization of a Human Cell Line (NK-92) With Phenotypical and Functional Characteristics of Activated Natural Killer Cells", Leukemia, 1994, vol. 8, No. 4, pp. 652-658.
Wang et al., "CD19: A Biomarkerfor B Cell Development, Lymphoma Diagnosis and Therapy", Experimental Hematology & Oncology, 2012, vol. 1, No. 36, pp. 1-7.
Haynes et al., "Redirecting Mouse CTL Against Colon Carcinoma: Superior Signaling Efficacy of Single-Chain Variable Domain Chimeras Containing TCR-zeta vs Fc epsilon RI-gamma", The Journal of Immunology, 2001, vol. 166, pp. 182-187.
Cartellieri et al., "Chimeric Antigen Receptor-Engineered T Cells for Immunotherapy of Cancer", Journal of Biomedicine and Biotechnology, 2010, vol. 2010, pp. 1-14.
Konstantinidis et al., "Targeting IL-2 to the End oplasmic Reticulum Confines Auto crine Growth Stimulation to NK-92 Cells", Experimental Hematology, 2005, vol. 33, pp. 159-164.
Sarcia-Sanchez et al., "Cytosine Deaminase Adenoviral Vector and 5-fluorocytosine Selectively Reduce Breast Cancer Cells 1 Million-Fold When They Contaminate Hemalopoielic Cells: A Potential Purging Method for Aulologous Transplantation", Blood, 1998, vol. 92, No. 2, pp. 672-682.
Stasi et al., "Inducible Apoptosis as a Safety Switch for Adoptive Cell Therapy", The New England journal of Medicine, 2011, vol. 365, No. 18, pp. 1673-1683.
Morgan Richard A, "Live and Let Die: A New Suicide Gene Therapy Moves to the Clinic", Molecular Therapy, Jan. 2012, vol. 20, No. 1, pp. 11-13.
Klingemann et al., "Interleukin-6 does not support interleukin-2 induced generation of human lymphokine-activated killer cells", Cancer Immunology, Immunotherapy, 1991, vol. 33, pp. 395-397.
Oelsner et al., "Continuously Expanding CAR NK-92 Cells Display Selective Cytotoxicity Against B-cell Leukemia and Lymphoma", Cytotherapy, 2016, vol. 19, No. 2, pp. 1-15.
Touati et al., "A Suicide Gene Therapy Combining the Improvement of Cyclophosphamide Tumor Cytotoxicity and the Development of an Anti-Tumor Immune Response", Current Gene Therapy, 2014, vol. 14, pp. 236-246.
Boissel et al., "Transfection with mRNA for CD19 specific chimeric antigen receptor restores NK cell mediated killing of CLL cells", Leukemia Research, 2009, vol. 33, pp. 1255-1259.
Boissel et al., "Comparison of mRNA and lentiviral based transfection of natural killer cells with chimeric antigen receptors recognizing lymphoid antigens", Leukemia & Lymphoma, May 2012, vol. 53, No. 5, pp. 958-965.
Boissel et al., "Relargeting NK-92 cells by means of CD19- and CD20-specific chimeric antigen receptors compares favorably with antibody-dependent cellular cytotoxicity", OncoImmunology, 2013, vol. 2, No. 10, 9 pages.
Romanski et al., "CD19-CAR engineered NK-92 cells are sufficient to overcome NK cell resistance in B-cellmalignancies", J Cell Mal Med, 2016, vol. 20, No. 7, pp. 1287-1294.
Suck et al., "NK-92: an 'off-the-shelf therapeutic' for adoptive natural killer cell-based cancer immunotherapy", Cancer Immunol Immunother, 2015, vol. 65, No. 4, 8 pages.
Non-Final Rejection received for U.S. Appl. No. 16/529,251 dated Mar. 23, 2020, 16 pages.
Notice of Allowance received for U.S. Appl. No. 16/529,251 dated Jul. 1, 2020, 12 pages.
Notice of Allowance received for U.S. Appl. No. 16/529,251 dated Jul. 6, 2020, 30 pages.
First Examination Report received for Israel Patent Application Serial No. 277413 dated Jan. 15, 2022, 12 pages. (Including English Translation).
Office Action received for Canadian Patent Application Serial No. 3092709 dated Sep. 16, 2021, 11 pages.
International Preliminary Report on Patentability Chapter I received for PCT Application Serial No. PCT/US2019/044691, dated May 14, 2021, 9 pages.
Notice of Allowance received for Canadian Patent Application Serial No. 3,092,709 dated Sep. 27, 2022, 1 page.
Office Action received for Israel Patent Application Serial No. 277413 dated Nov. 24, 2022, 9 pages. (Including English Translation).
Request for the Submission of an Opinion received for the Korean Patent Application Serial No. 10-2020-7028888 dated Jan. 27, 2023, 9 pages. (Including English Translation).
Reconsideration Examination Report received for the Japanese Patent Application Serial No. 2020-556293 dated Feb. 21, 2023, 9 pages. (Including English Translation).
Re-Transference to the Board of Appeal Trial received for the Japanese Patent Application Serial No. 2020-556293 dated Feb. 24, 2023, 2 pages. (Including English Translation).
First Office Action issued for CN Application No. 201980023744.6 dated Aug. 26, 2023, 17 pages (including English Translation).
First Office Action issued for JP Application No. 2022-181212 dated Oct. 24, 2023, 06 pages (including English.
Second Notice of Final Rejection issued for KR Application No. 10-2020-7028888 dated Oct. 31, 2023, 06 pages (including English Translation).
First Office Action issued for KR Application No. 10-2023-7035191 dated Nov. 27, 2023, 08 pages (including English Translation).
Notice of Reasons for Refusal received for Japanese Patent Application Serial No. 2020-556293 dated Dec. 24, 2021, 6 pages. (Including English Translation).
Second Office Action issued for CN Application No. 201980023744.6 dated Jun. 28, 2024, 20 pages (including English Translation).

* cited by examiner

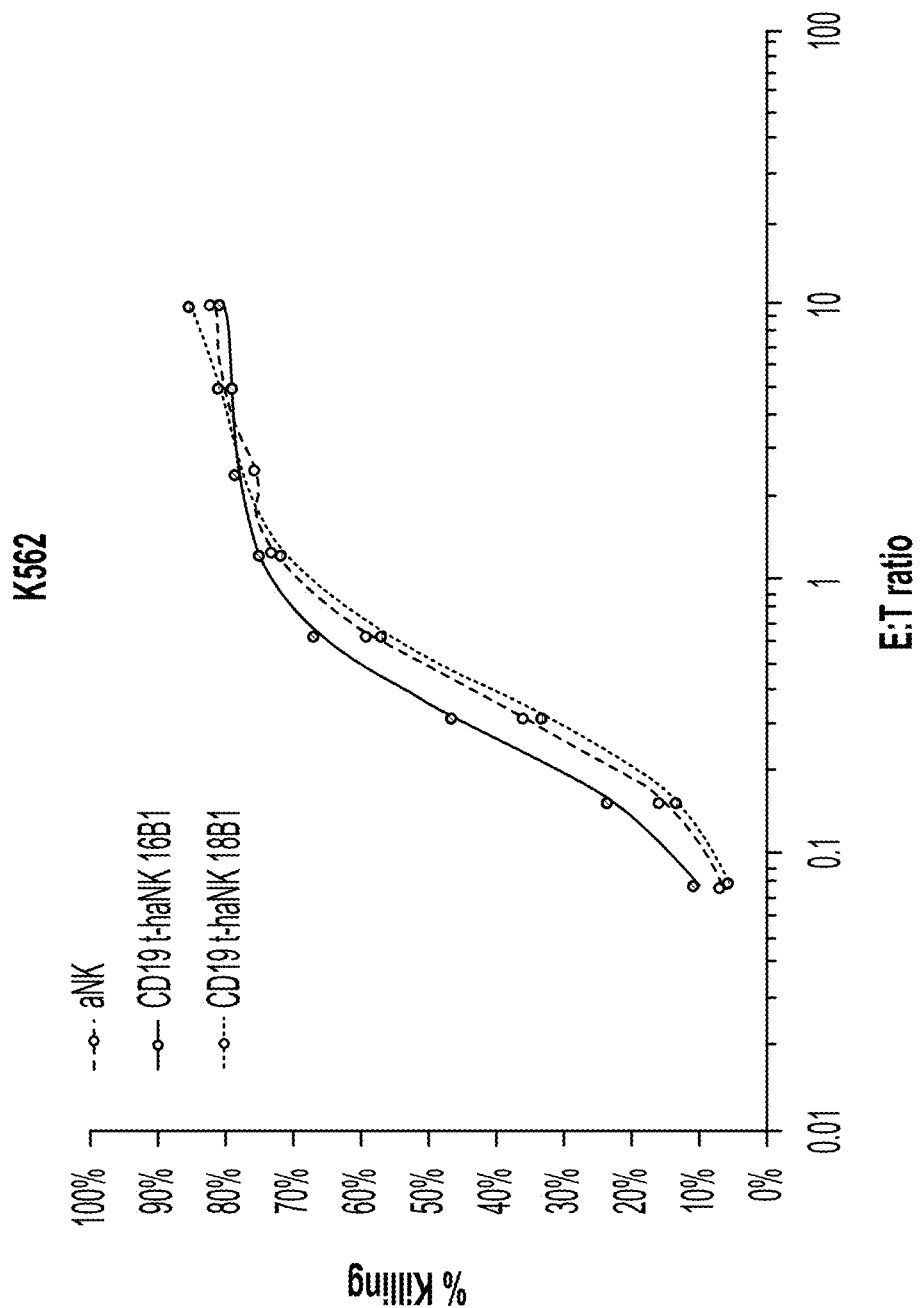

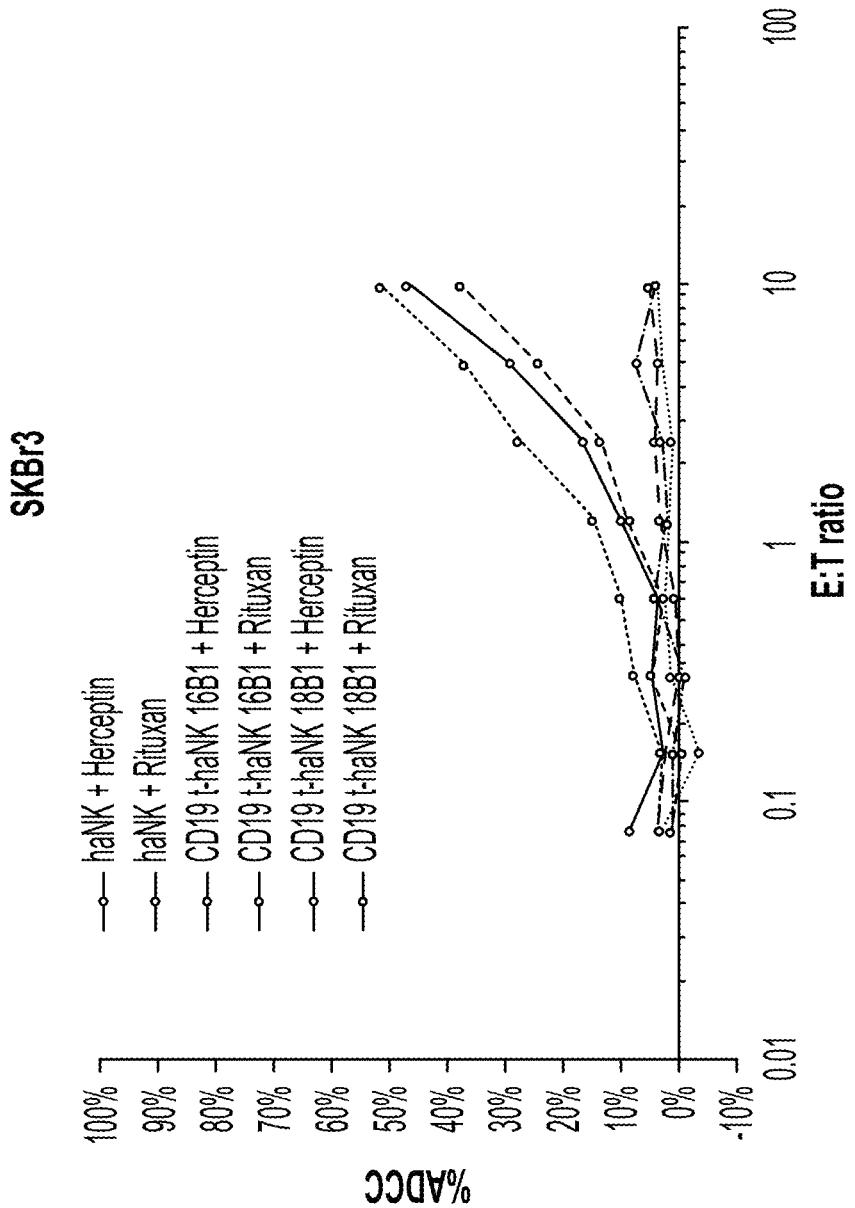

SEQUENCE LISTING

```
<160> NUMBER OF SEQ ID NOS: 15

<210> SEQ ID NO 1
<211> LENGTH: 236
<212> TYPE: PRT
<213> ORGANISM: Artificial Sequence
<220> FEATURE:
<223> OTHER INFORMATION: Laboratory sequence

<400> SEQUENCE: 1

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asp
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
    130                 135                 140

Thr Leu Lys Asp Ser Gly Ser Tyr Phe Cys Arg Gly Leu Phe Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Phe Pro Pro Gly Tyr Gln Val Ser
```

```
                    180                 185                 190
Phe Cys Leu Val Met Val Leu Leu Phe Ala Val Asp Thr Gly Leu Tyr
        195                 200                 205

Phe Ser Val Lys Thr Asn Ile Arg Ser Ser Thr Arg Asp Trp Lys Asp
        210                 215                 220

His Lys Phe Lys Trp Arg Lys Asp Pro Gln Asp Lys
225                 230                 235

<210> SEQ ID NO 2
<211> LENGTH: 236
<212> TYPE: PRT
<213> ORGANISM: Artificial Sequence
<220> FEATURE:
<223> OTHER INFORMATION: laboratory sequence

<400> SEQUENCE: 2

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asp
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
    130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Phe Pro Pro Gly Tyr Gln Val Ser
            180                 185                 190

Phe Cys Leu Val Met Val Leu Leu Phe Ala Val Asp Thr Gly Leu Tyr
        195                 200                 205

Phe Ser Val Lys Thr Asn Ile Arg Ser Ser Thr Arg Asp Trp Lys Asp
        210                 215                 220

His Lys Phe Lys Trp Arg Lys Asp Pro Gln Asp Lys
225                 230                 235

<210> SEQ ID NO 3
<211> LENGTH: 254
<212> TYPE: PRT
<213> ORGANISM: Artificial Sequence
<220> FEATURE:
<223> OTHER INFORMATION: laboratory sequence

<400> SEQUENCE: 3

Met Trp Gln Leu Leu Leu Pro Thr Ala Leu Leu Leu Leu Val Ser Ala
1               5                   10                  15
```

```
Gly Met Arg Thr Glu Asp Leu Pro Lys Ala Val Val Phe Leu Glu Pro
             20                  25                  30

Gln Trp Tyr Arg Val Leu Glu Lys Asp Ser Val Thr Leu Lys Cys Gln
         35                  40                  45

Gly Ala Tyr Ser Pro Glu Asp Asn Ser Thr Gln Trp Phe His Asn Glu
     50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 4
<211> LENGTH: 254
<212> TYPE: PRT
<213> ORGANISM: Artificial Sequence
<220> FEATURE:
<223> OTHER INFORMATION: laboratory made

<400> SEQUENCE: 4

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
             20                  25                  30

Gln Trp Tyr Arg Val Leu Glu Lys Asp Ser Val Thr Leu Lys Cys Gln
         35                  40                  45

Gly Ala Tyr Ser Pro Glu Asp Asn Ser Thr Gln Trp Phe His Asn Glu
     50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125
```

His Ser Trp Lys Asn Thr Ala Leu His Lys Val Thr Tyr Leu Gln Asn
            130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 5
<211> LENGTH: 765
<212> TYPE: DNA
<213> ORGANISM: Artificial Sequence
<220> FEATURE:
<223> OTHER INFORMATION: laboratory made

<400> SEQUENCE: 5
atgtggcagc tgctcctccc aactgctctg ctacttctag tttcagctgg catgcggact     60
gaagatctcc caaggctgt ggtgttcctg gagcctcaat ggtacagggt gctcgagaag    120
gacagtgtga ctctgaagtg ccagggagcc tactcccctg aggacaattc cacacagtgg    180
tttcacaatg agagcctcat ctcaagccag gcctcgagct acttcattga cgctgccaca    240
gtcgacgaca gtggagagta caggtgccag acaaacctct ccaccctcag tgacccggtg    300
cagctagaag tccatatcgg ctggctgttg ctccaggccc ctcggtgggt gttcaaggag    360
gaagacccta ttcacctgag gtgtcacagc tggaagaaca ctgctctgca taaggtcaca    420
tatttacaga tggcaaagg caggaagtat tttcatcata attctgactt ctacattcca    480
aaagccacac tcaaagacag cggctcctac ttctgcaggg ggcttttttgg gagtaaaaat    540 gtgtcttcag agactgtgaa catcaccatc actcaaggtt tggcagtgtc aaccatctca    600
tcattctttc cacctgggta ccaagtctct ttctgcttgg tgatggtact ccttttttgca    660 gtggacacag gactatatt tctctgtgaag acaaacattc gaagctcaac aagagactgg    720
aaggaccata aatttaaatg gagaaaggac cctcaagaca aatga    765

<210> SEQ ID NO 6
<211> LENGTH: 153
<212> TYPE: PRT
<213> ORGANISM: Artificial Sequence
<220> FEATURE:
<223> OTHER INFORMATION: laboratory sequence

<400> SEQUENCE: 6

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 7
<211> LENGTH: 160
<212> TYPE: PRT
<213> ORGANISM: Artificial Sequence
<220> FEATURE:
<223> OTHER INFORMATION: laboratory sequence

<400> SEQUENCE: 7

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Ser Glu Lys Asp Glu Leu
145                 150                 155                 160

<210> SEQ ID NO 8
<211> LENGTH: 66
<212> TYPE: DNA
<213> ORGANISM: Artificial Sequence
<220> FEATURE:
<223> OTHER INFORMATION: laboratory sequence

<400> SEQUENCE: 8
ggaagcggag ctactaactt cagcctgctg aagcaggctg agacgtgga ggagaaccct      60 ggacct                                                               66

<210> SEQ ID NO 9
<211> LENGTH: 813
<212> TYPE: DNA

<213> ORGANISM: Artificial Sequence
<220> FEATURE:
<223> OTHER INFORMATION: laboratory sequence

<400> SEQUENCE: 9

```
atggactgga tctggcggat tctgtttctc gtgggagctg ccacaggcgc tcattctgct      60
cagcctgccg atatccagat gacccagaca acaagcagcc tgagcgcctc tctgggcgat     120
agagtgacaa tcagctgcag agccagccag gacatcagca agtacctgaa ctggtatcag     180
cagaaacccg acggcaccgt gaagctgctg atctaccaca caagcagact gcacagcggc     240
gtgccaagca gatttctgg cagcggcagc ggcaccgatt acagcctgac catcagcaac     300
ctgaacagg aagatatcgc tacctacttc tgtcagcagg gcaacaccct gccttacacc     360
tttggcggcg gaacaaagct ggaactgaaa agaggcggcg gaggaagcgg aggcggagga     420
tctgggggcg gaggctctgg cggaggggga tctgaagtgc agctgcagca gtctggacct     480
ggactggtgg ctccttctca gtccctgtct gtgacctgta cagtgtctgg cgtgtccctg     540
cctgattacg gcgtgtcctg gatcagacag cctcccagaa aaggcctgga atggctggga     600
gtgatctggg gcagcgagac aacctactac aacagcgccc tgaagtcccg gctgaccatc     660
atcaaggaca cagcaagag ccaggtgttc ctgaagatga cagcctgca gaccgacgac     720
accgccatct actactgcgc caagcactac tactacggcg gcagctacgc catggattat     780
tggggccagg gcaccaccgt gacagtgtca tct                                  813
```

<210> SEQ ID NO 10
<211> LENGTH: 271
<212> TYPE: PRT
<213> ORGANISM: Artificial Sequence
<220> FEATURE:
<223> OTHER INFORMATION: laboratory sequence

<400> SEQUENCE: 10

```
Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Leu Lys Arg Gly Gly Gly Gly Ser Gly Gly Gly Gly Ser Gly Gly Gly
    130                 135                 140

Gly Ser Gly Gly Gly Gly Ser Glu Val Gln Leu Gln Gln Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190
```

Arg Lys Gly Leu Glu Trp Leu Gly Val Ile Trp Gly Ser Glu Thr Thr
        195                 200                 205

Tyr Tyr Asn Ser Ala Leu Lys Ser Arg Leu Thr Ile Ile Lys Asp Asn
        210                 215                 220

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Tyr Gly Gly Ser Tyr
                245                 250                 255

Ala Met Asp Tyr Trp Gly Gln Gly Thr Thr Val Thr Val Ser Ser
            260                 265                 270

<210> SEQ ID NO 11
<211> LENGTH: 1221
<212> TYPE: DNA
<213> ORGANISM: Artificial Sequence
<220> FEATURE:
<223> OTHER INFORMATION: laboratory sequence

<400> SEQUENCE: 11
atggactgga tctggcggat tctgtttctc gtgggagctg ccacaggcgc tcattctgct    60
cagcctgccg atatccagat gacccagaca acaagcagcc tgagcgcctc tctgggcgat   120
agagtgacaa tcagctgcag agccagccag acatcagca agtacctgaa ctggtatcag   180
cagaaacccg acggcaccgt gaagctgctg atctaccaca aagcagact gcacagcggc   240
gtgccaagca gatttctgg cagcggcagc ggcaccgatt acagcctgac catcagcaac   300
ctggaacagg aagatatcgc tacctacttc tgtcagcagg caacaccct gccttacacc   360
tttggcggcg gaacaaagct ggaactgaaa agaggcggcg gaggaagcgg aggcggagga   420
tctggggcg gaggctctgg cggagggga tctgaagtgc agctgcagca gtctggacct   480
ggactggtgg ctccttctca gtccctgtct gtgacctgta cagtgtctgg cgtgtccctg   540
cctgattacg gcgtgtcctg gatcagacag cctcccagaa aaggcctgga atggctggga   600
gtgatctggg gcagcgagac aacctactac aacagcgccc tgaagtcccg gctgaccatc   660
atcaaggaca cagcaagag ccaggtgttc ctgaagatga cagcctgca gaccgacgac   720
accgccatct actactgcgc caagcactac tactacggcg gcagctacgc catggattat   780
tggggccagg gcaccaccgt gacagtgtca tctgcggccg cgctgagcaa cagcatcatg   840
tacttcagcc acttcgtgcc tgtgttcctg cctgccaagc ctacaacaac accagcccct   900
agacctccaa cccctgcccc tacaattgcc tctcagcctc tgtctctgag gcccgaagct   960
tgtagacctg ctgctggcgg agctgtgcac accagaggac tggatttcgc ctgcttttgg  1020
gtgctggtgg tcgtgggcgg agtgctggct tgttattctc tgctggtcac cgtggccttc  1080
atcatctttt gggtccgact gaagatccag gtccgaaagg ccgccatcac cagctacgag  1140
aagtctgatg gcgtgtacac cggcctgagc accagaaacc aggaaaccta cgagacactg  1200
aagcacgaga gccccccca g                                             1221

<210> SEQ ID NO 12
<211> LENGTH: 407
<212> TYPE: PRT
<213> ORGANISM: Artificial Sequence
<220> FEATURE:
<223> OTHER INFORMATION: laboratory sequence

<400> SEQUENCE: 12

Met Asp Trp Ile Trp Arg Ile Leu Phe Leu Val Gly Ala Ala Thr Gly

```
1               5                    10                   15
Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
            35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
            115                 120                 125

Leu Lys Arg Gly Gly Gly Gly Ser Gly Gly Gly Gly Ser Gly Gly Gly
        130                 135                 140

Gly Ser Gly Gly Gly Gly Ser Glu Val Gln Leu Gln Gln Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190

Arg Lys Gly Leu Glu Trp Leu Gly Val Ile Trp Gly Ser Glu Thr Thr
        195                 200                 205

Tyr Tyr Asn Ser Ala Leu Lys Ser Arg Leu Thr Ile Ile Lys Asp Asn
210                 215                 220

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Tyr Gly Gly Ser Tyr
                245                 250                 255

Ala Met Asp Tyr Trp Gly Gln Gly Thr Thr Val Thr Val Ser Ser Ala
            260                 265                 270

Ala Ala Leu Ser Asn Ser Ile Met Tyr Phe Ser His Phe Val Pro Val
        275                 280                 285

Phe Leu Pro Ala Lys Pro Thr Thr Thr Pro Ala Pro Arg Pro Pro Thr
290                 295                 300

Pro Ala Pro Thr Ile Ala Ser Gln Pro Leu Ser Leu Arg Pro Glu Ala
305                 310                 315                 320

Cys Arg Pro Ala Ala Gly Gly Ala Val His Thr Arg Gly Leu Asp Phe
                325                 330                 335

Ala Cys Phe Trp Val Leu Val Val Val Gly Gly Val Leu Ala Cys Tyr
            340                 345                 350

Ser Leu Leu Val Thr Val Ala Phe Ile Ile Phe Trp Val Arg Leu Lys
        355                 360                 365

Ile Gln Val Arg Lys Ala Ala Ile Thr Ser Tyr Glu Lys Ser Asp Gly
370                 375                 380

Val Tyr Thr Gly Leu Ser Thr Arg Asn Gln Glu Thr Tyr Glu Thr Leu
385                 390                 395                 400

Lys His Glu Lys Pro Pro Gln
                405

<210> SEQ ID NO 13
```

<211> LENGTH: 6778
<212> TYPE: DNA
<213> ORGANISM: Artificial Sequence
<220> FEATURE:
<223> OTHER INFORMATION: laboratory sequence

<400> SEQUENCE: 13

| | | | | | |
|---|---|---|---|---|---|
| tgtatttaga | aaaataaaca | aatagggggtt | ccgcgcacat | ttccccgaaa | agtgccacct | 60 |
| gacgtcgacg | gatcgggaga | tctcccgatc | ccctatggtg | cactctcagt | acaatctgct | 120 |
| ctgatgccgc | atagttaagc | cagtatctgc | tccctgcttg | tgtgttggag | gtcgctgagt | 180 |
| agtgcgcgag | caaaatttaa | gctacaacaa | ggcaaggctt | gaccgacaat | tgcatgaaga | 240 |
| atctgcttag | ggttaggcgt | tttgcgctgc | ttcgggatcc | gctgaccaaa | agagcaccaa | 300 |
| aggcgccctg | accttcagcc | cctacctgcg | ctccggtgcc | cgtcagtggg | cagagcgcac | 360 |
| atcgcccaca | gtccccgaga | agttgggggg | aggggtcggc | aattgaaccg | gtgcctagag | 420 |
| aaggtggcgc | ggggtaaact | gggaaagtga | tgtcgtgtac | tggctccgcc | ttttccccga | 480 |
| gggtgggggga | gaaccgtata | taagtgcagt | agtcgccgtg | aacgttcttt | ttcgcaacgg | 540 |
| gtttgccgcc | agaacacagg | taagtgccgt | gtgtggttcc | cgcgggcctg | gcctctttac | 600 |
| gggttatggc | ccttgcgtgc | cttgaattac | ttccacctgg | ctgcagtacg | tgattcttga | 660 |
| tcccgagctt | cgggttggaa | gtgggtggga | gagttcgagg | ccttgcgctt | aaggagcccc | 720 |
| ttcgcctcgt | gcttgagttg | aggcctggcc | tgggcgctgg | ggccgccgcg | tgcgaatctg | 780 |
| gtggcacctt | cgcgcctgtc | tcgctgcttt | cgataagtct | ctagccattt | aaaattttg | 840 |
| atgacctgct | gcgacgcttt | ttttctggca | agatagtctt | gtaaatgcgg | gccaagatct | 900 |
| gcacactggt | atttcggttt | ttggggccgc | gggcggcgac | ggggcccgtg | cgtcccagcg | 960 |
| cacatgttcg | gcgaggcggg | gcctgcgagc | gcggccaccg | agaatcggac | ggggggtagtc | 1020 |
| tcaagctggc | cggcctgctc | tggtgcctgg | cctcgcgccg | ccgtgtatcg | ccccgccctg | 1080 |
| ggcggcaagg | ctggcccggt | cggcaccagt | tgcgtgagcg | gaaagatggc | cgcttccccgg | 1140 |
| ccctgctgca | gggagctcaa | aatggaggac | gcggcgctcg | ggagagcggg | cgggtgagtc | 1200 |
| acccacacaa | aggaaaaggg | cctttccgtc | ctcagccgtc | gcttcatgtg | actccacgga | 1260 |
| gtaccgggcg | ccgtccaggc | acctcgatta | gttctcgagc | ttttggagta | cgtcgtcttt | 1320 |
| aggttgggggg | gaggggtttt | atgcgatgga | gtttccccac | actgagtggg | tggagactga | 1380 |
| agttaggcca | gcttggcact | tgatgtaatt | ctccttggaa | tttgcccttt | ttgagtttgg | 1440 |
| atcttggttc | attctcaagc | ctcagacagt | ggttcaaagt | tttttttcttc | catttcaggt | 1500 |
| gtcgtgataa | tacgactcac | tatagggaga | cccaagctgg | aattcgccac | catggactgg | 1560 |
| atctggcgga | ttctgtttct | cgtgggagct | gccacaggcg | ctcattctgc | tcagcctgcc | 1620 |
| gatatccaga | tgacccagac | aacaagcagc | ctgagcgcct | ctctgggcga | tagagtgaca | 1680 |
| atcagctgca | gagccagcca | ggacatcagc | aagtacctga | actggtatca | gcagaaaccc | 1740 |
| gacggcaccg | tgaagctgct | gatctaccac | acaagcagac | tgcacagcgg | cgtgccaagc | 1800 |
| agattttctg | gcagcggcag | cggcaccgat | tacagcctga | ccatcagcaa | cctggaacag | 1860 |
| gaagatatcg | ctacctactt | ctgtcagcag | ggcaacaccc | tgccttacac | ctttggcggc | 1920 |
| ggaacaaagc | tggaactgaa | aagaggcggc | ggaggaagcg | gaggcggagg | atctgggggc | 1980 |
| ggaggctctg | gcggaggggg | atctgaagtg | cagctgcagc | agtctggacc | tggactggtg | 2040 |
| gctccttctc | agtccctgtc | tgtgacctgt | acagtgtctg | gcgtgtccct | gcctgattac | 2100 |
| ggcgtgtcct | ggatcagaca | gcctccccag | aaaggcctgg | aatggctggg | agtgatctgg | 2160 |

```
ggcagcgaga caacctacta caacagcgcc ctgaagtccc ggctgaccat catcaaggac    2220
aacagcaaga gccaggtgtt cctgaagatg aacagcctgc agaccgacga caccgccatc    2280
tactactgcg ccaagcacta ctactacggc ggcagctacg ccatggatta ttggggccag    2340
ggcaccaccg tgacagtgtc atctgcggcc gcgctgagca acagcatcat gtacttcagc    2400
cacttcgtgc ctgtgttcct gcctgccaag cctacaacaa caccagcccc tagacctcca    2460 accccctgccc ctacaattgc ctctcagcct ctgtctctga ggcccgaagc ttgtagacct    2520
gctgctggcg gagctgtgca caccagagga ctggatttcg cctgcttttg ggtgctggtg    2580
gtcgtgggcg gagtgctggc ttgttattct ctgctggtca ccgtggcctt catcatcttt    2640
tgggtccgac tgaagatcca ggtccgaaag gccgccatca ccagctacga agtctgat     2700 ggcgtgtaca ccggcctgag caccagaaac caggaaacct acgagacact gaagcacgag    2760
aagccccccc agggaagcgg agctactaac ttcagcctgc tgaagcaggc tggagacgtg    2820
gaggagaacc ctggacctat gtggcagctg ctgctgccta cagctctcct gctgctggtg    2880
tccgccggca tgagaaccga ggatctgcct aaggccgtgg tgttcctgga accccagtgg    2940
tacagagtgc tggaaaagga cagcgtgacc ctgaagtgcc agggcgccta cagccccgag    3000
gacaatagca cccagtggtt ccacaacgag agcctgatca gcagccaggc cagcagctac    3060
ttcatcgacg ccgccaccgt ggacgacagc ggcgagtata gatgccagac caacctgagc    3120
accctgagcg accccgtgca gctggaagtg cacatcggat ggctgctgct gcaggccccc    3180
agatgggtgt tcaaagaaga ggaccccatc cacctgagat gccactcttg gaagaacacc    3240
gccctgcaca aagtgaccta cctgcagaac ggcaagggca gaagtgtactt ccaccacaac    3300 agcgacttct acatccccaa ggccaccctg aaggactccg gctcctactt ctgcagaggc    3360
ctcgtgggca gcaagaacgt gtccagcgag acagtgaaca tcaccatcac ccagggcctg    3420
gccgtgtcta ccatcagcag ctttttccca cccggctacc aggtgtcctt ctgcctcgtg    3480
atggtgctgc tgttcgccgt ggacaccggc ctgtacttca gcgtgaaaac aaacatcaga    3540
agcagcaccc gggactggaa ggaccacaag ttcaagtggc ggaaggaccc ccaggacaag    3600
tgaaattccg cccctctccc ccccccccct ctccctcccc ccccctaac gttactggcc    3660 gaagccgctt ggaataaggc cggtgtgcgt ttgtctatat gttattttcc accatattgc    3720
cgtcttttgg caatgtgagg gcccggaaac ctggccctgt cttcttgacg agcattccta    3780
ggggtctttc ccctctcgcc aaaggaatgc aaggtctgtt gaatgtcgtg aaggaagcag    3840
ttcctctgga agcttcttga agacaaacaa cgtctgtagc gaccctttgc aggcagcgga    3900 acccccacc tggcgacagg tgcctctgcg gccaaaagcc acgtgtataa gatacacctg    3960 caaaggcgg acaaccccag tgccacgttg tgagttggat agttgtggaa agagtcaaat    4020
ggctctcctc aagcgtattc aacaagggc tgaaggatgc ccagaaggta ccccattgta    4080
tgggatctga tctggggcct cggtgcacat gctttacatg tgtttagtcg aggttaaaaa    4140
aacgtctagg ccccccgaac cacggggacg tggttttcct ttgaaaaaca cgataaccgc    4200
caccatgtac cggatgcagc tgctgagctg tatcgccctg tctctggccc tcgtgaccaa    4260
cagcgcccct accagcagca gcaccaagaa aacccagctg cagctggaac atctgctgct    4320
ggacctgcag atgatcctga acggcatcaa caactacaag aaccccaagc tgacccggat    4380
gctgaccttc aagttctaca tgcccaagaa ggccaccgaa ctgaaacatc tgcagtgcct    4440
ggaagaggaa ctgaagcccc tggaagaagt gctgaacctg gcccagagca agaacttcca    4500
```

```
cctgaggccc agggacctga tcagcaacat caacgtgatc gtgctggaac tgaaaggcag    4560
cgagacaacc ttcatgtgcg agtacgccga cgagacagct accatcgtgg aatttctgaa    4620
ccggtggatc accttctgcc agagcatcat cagcaccctg accggctccg agaaggacga    4680
gctgtgagcg gccgcccgct gatcagcctc gaacgagatt tcgattccac cgccgccttc    4740
tatgaaaggt tgggcttcgg aatcgttttc cgggacgccg gctggatgat cctccagcgc    4800
ggggatctca tgctggagtt cttcgcccac cccaacttgt ttattgcagc ttataatggt    4860
tacaaataaa gcaatagcat cacaaatttc acaaataaag cattttttc actgcattct    4920
agttgtggtt tgtccaaact catcaatgta tcttatcatg tctgtgcggt gggctctatg    4980
gcttctgagg cggaaagaac cagctggggc tctaggggt atccccggat cctgagcaaa    5040
aggccagcaa aaggccagga accgtaaaaa ggccgcgttg ctggcgtttt tccataggct    5100
ccgccccct gacgagcatc acaaaaatcg acgctcaagt cagaggtggc gaaacccgac    5160
aggactataa agataccagg cgtttccccc tggaagctcc ctcgtgcgct ctcctgttcc    5220
gaccctgccg cttaccggat acctgtccgc ctttctccct tcgggaagcg tggcgctttc    5280
tcatagctca cgctgtaggt atctcagttc ggtgtaggtc gttcgctcca agctgggctg    5340
tgtgcacgaa ccccccgttc agcccgaccg ctgcgcctta tccggtaact atcgtcttga    5400
gtccaacccg gtaagacacg acttatcgcc actggcagca gccactggta acaggattag    5460
cagagcgagg tatgtaggcg gtgctacaga gttcttgaag tggtggccta actacggcta    5520
cactagaaga acagtatttg gtatctgcgc tctgctgaag ccagttacct tcggaaaaag    5580
agttggtagc tcttgatccg gcaaacaaac caccgctggt agcggtggtt tttttgtttg    5640
caagcagcag attacgcgca gaaaaaaagg atcctcttga tcttttctac    5700
ggggtctgac gctcagtgga acgaaaactc acgttaaggg attttggtca tgagattatc    5760
aaaaaggatc ttcacctaga tccttttaaa ttaaaaatga agttttaaat caatctaaag    5820
tatatatgag taaacttggt ctgacagtta ccaatgctta atcagtgagg cacctatctc    5880
agcgatctgt ctatttcgtt catccatagt tgcctgactc ccgtcgtgt agataactac    5940
gatacgggag ggcttaccat ctggccccag tgctgcaatg ataccgcgag aaccacgctc    6000
accggctcca gatttatcag caataaacca gccagccgga agggccgagc gcagaagtgg    6060
tcctgcaact ttatccgcct ccatccagtc tattaattgt tgccgggaag ctagagtaag    6120
tagttcgcca gttaatagtt tgcgcaacgt tgttgccatt gctacaggca tcgtggtgtc    6180
acgctcgtcg tttggtatgg cttcattcag ctccggttcc caacgatcaa ggcgagttac    6240
atgatccccc atgttgtgca aaaaagcggt tagctccttc ggtcctccga tcgttgtcag    6300
aagtaagttg gccgcagtgt tatcactcat ggttatggca gcactgcata attctcttac    6360
tgtcatgcca tccgtaagat gcttttctgt gactggtgag tactcaacca agtcattctg    6420
agaatagtgt atgcggcgac cgagttgctc ttgcccggcg tcaatacggg ataataccgc    6480
gccacatagc agaactttaa aagtgctcat cattggaaaa cgttcttcgg ggcgaaaact    6540
ctcaaggatc ttaccgctgt tgagatccag ttcgatgtaa cccactcgtg cacccaactg    6600
atcttcagca tcttttactt tcaccagcgt ttctgggtga gcaaaaacag gaaggcaaaa    6660
tgccgcaaaa aagggaataa gggcgacacg gaaatgttga atactcatac tcttcctttt    6720
tcaatattat tgaagcattt atcagggtta ttgtctcatg agcggataca tatttgaa      6778
```

<210> SEQ ID NO 14
<211> LENGTH: 683

<212> TYPE: PRT
<213> ORGANISM: Artificial Sequence
<220> FEATURE:
<223> OTHER INFORMATION: laboratory sequence

<400> SEQUENCE: 14

```
Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Leu Lys Arg Gly Gly Gly Gly Ser Gly Gly Gly Gly Ser Gly Gly Gly
    130                 135                 140

Gly Ser Gly Gly Gly Gly Ser Glu Val Gln Leu Gln Gln Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190

Arg Lys Gly Leu Glu Trp Leu Gly Val Ile Trp Gly Ser Glu Thr Thr
        195                 200                 205

Tyr Tyr Asn Ser Ala Leu Lys Ser Arg Leu Thr Ile Ile Lys Asp Asn
    210                 215                 220

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Gly Gly Ser Tyr
                245                 250                 255

Ala Met Asp Tyr Trp Gly Gln Gly Thr Thr Val Thr Val Ser Ser Ala
            260                 265                 270

Ala Ala Leu Ser Asn Ser Ile Met Tyr Phe Ser His Phe Val Pro Val
        275                 280                 285

Phe Leu Pro Ala Lys Pro Thr Thr Thr Pro Ala Pro Arg Pro Pro Thr
    290                 295                 300

Pro Ala Pro Thr Ile Ala Ser Gln Pro Leu Ser Leu Arg Pro Glu Ala
305                 310                 315                 320

Cys Arg Pro Ala Ala Gly Gly Ala Val His Thr Arg Gly Leu Asp Phe
                325                 330                 335

Ala Cys Phe Trp Val Leu Val Val Val Gly Gly Val Leu Ala Cys Tyr
            340                 345                 350

Ser Leu Leu Val Thr Val Ala Phe Ile Ile Phe Trp Val Arg Leu Lys
        355                 360                 365

Ile Gln Val Arg Lys Ala Ala Ile Thr Ser Tyr Glu Lys Ser Asp Gly
    370                 375                 380
```

Val Tyr Thr Gly Leu Ser Thr Arg Asn Gln Glu Thr Tyr Glu Thr Leu
385                 390                 395                 400

Lys His Glu Lys Pro Pro Gln Gly Ser Gly Ala Thr Asn Phe Ser Leu
            405                 410                 415

Leu Lys Gln Ala Gly Asp Val Glu Glu Asn Pro Gly Pro Met Trp Gln
        420                 425                 430

Leu Leu Leu Pro Thr Ala Leu Leu Leu Val Ser Ala Gly Met Arg
        435                 440                 445

Thr Glu Asp Leu Pro Lys Ala Val Val Phe Leu Glu Pro Gln Trp Tyr
    450                 455                 460

Arg Val Leu Glu Lys Asp Ser Val Thr Leu Lys Cys Gln Gly Ala Tyr
465                 470                 475                 480

Ser Pro Glu Asp Asn Ser Thr Gln Trp Phe His Asn Glu Ser Leu Ile
                485                 490                 495

Ser Ser Gln Ala Ser Ser Tyr Phe Ile Asp Ala Ala Thr Val Asp Asp
            500                 505                 510

Ser Gly Glu Tyr Arg Cys Gln Thr Asn Leu Ser Thr Leu Ser Asp Pro
        515                 520                 525

Val Gln Leu Glu Val His Ile Gly Trp Leu Leu Leu Gln Ala Pro Arg
    530                 535                 540

Trp Val Phe Lys Glu Glu Asp Pro Ile His Leu Arg Cys His Ser Trp
545                 550                 555                 560

Lys Asn Thr Ala Leu His Lys Val Thr Tyr Leu Gln Asn Gly Lys Gly
                565                 570                 575

Arg Lys Tyr Phe His His Asn Ser Asp Phe Tyr Ile Pro Lys Ala Thr
            580                 585                 590

Leu Lys Asp Ser Gly Ser Tyr Phe Cys Arg Gly Leu Val Gly Ser Lys
        595                 600                 605

Asn Val Ser Ser Glu Thr Val Asn Ile Thr Ile Thr Gln Gly Leu Ala
    610                 615                 620

Val Ser Thr Ile Ser Ser Phe Phe Pro Pro Gly Tyr Gln Val Ser Phe
625                 630                 635                 640

Cys Leu Val Met Val Leu Leu Phe Ala Val Asp Thr Gly Leu Tyr Phe
                645                 650                 655

Ser Val Lys Thr Asn Ile Arg Ser Ser Thr Arg Asp Trp Lys Asp His
            660                 665                 670

Lys Phe Lys Trp Arg Lys Asp Pro Gln Asp Lys
        675                 680

<210> SEQ ID NO 15
<211> LENGTH: 160
<212> TYPE: PRT
<213> ORGANISM: Artificial Sequence
<220> FEATURE:
<223> OTHER INFORMATION: laboratory sequence

<400> SEQUENCE: 15

Met Tyr Arg Met Gln Leu Leu Ser Cys Ile Ala Leu Ser Leu Ala Leu
1                   5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

-continued

| | | | | | | | | | | | | | | | |
|---|---|---|---|---|---|---|---|---|---|---|---|---|---|---|---|
| Tyr | Met | Pro | Lys | Lys | Ala | Thr | Glu | Leu | Lys | His | Leu | Gln | Cys | Leu | Glu |
| 65 | | | | 70 | | | | | 75 | | | | | | 80 |
| Glu | Glu | Leu | Lys | Pro | Leu | Glu | Glu | Val | Leu | Asn | Leu | Ala | Gln | Ser | Lys |
| | | | | 85 | | | | | 90 | | | | | 95 | |
| Asn | Phe | His | Leu | Arg | Pro | Arg | Asp | Leu | Ile | Ser | Asn | Ile | Asn | Val | Ile |
| | | | 100 | | | | | 105 | | | | | 110 | | |
| Val | Leu | Glu | Leu | Lys | Gly | Ser | Glu | Thr | Thr | Phe | Met | Cys | Glu | Tyr | Ala |
| | | 115 | | | | | 120 | | | | | 125 | | | |
| Asp | Glu | Thr | Ala | Thr | Ile | Val | Glu | Phe | Leu | Asn | Arg | Trp | Ile | Thr | Phe |
| | 130 | | | | | 135 | | | | | 140 | | | | |
| Cys | Gln | Ser | Ile | Ile | Ser | Thr | Leu | Thr | Gly | Ser | Glu | Lys | Asp | Glu | Leu |
| 145 | | | | | 150 | | | | | 155 | | | | | 160 |

ELIMINATION OF CD19-POSITIVE LYMPHOID MALIGNANCIES BY CD19-CAR EXPRESSING NK CELLS

This application is a divisional of US patent application with the Ser. No. 16/529,251, filed Aug. 1, 2019, which is now issued as U.S. Pat. No. 10,765,701. This application also claims priority to US provisional application with the Ser. No. 62/753,719, filed Oct. 31, 2018.

SEQUENCE LISTING

The content of the ASCII text file of the sequence listing named 104077_0008PCT Seq_ST25, which is 38 KB in size was created on Jul. 15, 2019 and electronically submitted via EFS-Web along with the present application, and is incorporated by reference in its entirety.

FIELD OF THE INVENTION

The field of the invention is engineered cells in relation to cancer therapy.

BACKGROUND

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Natural killer (NK) cells are cytotoxic lymphocytes that constitute a major component of the innate immune system. Natural killer (NK) cells, generally representing about 10-15% of circulating lymphocytes, bind and kill targeted cells, including virus-infected cells and many malignant cells, non-specifically with regard to antigen and without prior immune sensitization. Herberman et al., Science 214: 24 (1981). Killing of targeted cells occurs by inducing cell lysis. NK cells used for autologous NK cell transplants are isolated from the peripheral blood lymphocyte ("PBL") fraction of blood from the subject, expanded in cell culture in order to obtain sufficient numbers of cells, and then re-infused into the subject. Such autologous NK cells have shown some effectiveness in in vivo treatment. However, such therapy is limited to autologous contexts, and further complicated by the fact that not all NK cells are cytolytic.

NK-92® is a cytolytic cancer cell line which was discovered in the blood of a subject suffering from a non-Hodgkins lymphoma and then immortalized in vitro. NK-92® cells are derived from NK cells, but lack the major inhibitory receptors that are displayed by normal NK cells, while retaining the majority of the activating receptors. NK-92® cells do not, however, attack normal cells nor do they elicit an unacceptable immune rejection response in humans. Characterization of the NK-92® cell line is disclosed in WO 1998/049268 and U.S. Patent Application Publication No. 2002-0068044. NK-92® cells have been evaluated as a therapeutic agent in the treatment of certain cancers.

SUMMARY

In some embodiments, this disclosure provides a NK-92® cell expressing a CD19 CAR and a Fc receptor. In some embodiments, the NK-92® cell comprises a multi-cistronic construct that encodes the CD19 CAR and the Fc receptor. In some embodiments, the Fc receptor is a CD16. In some embodiments, the Fc receptor comprises SEQ ID NO: 2. In some embodiments, the multi-cistronic transgene further comprises a sequence that encodes an IL-2 or a variant thereof. In some embodiments, the IL-2 variant is erIL-2. In some embodiments, the coding sequences for one or more of the CD19 CAR, the Fc receptor, or erIL-2 are codon-optimized for expression in a human system.

In some embodiments, NK-92® cell is capable of killing a CD19-expressing cell, for example, a tumor cell. In some embodiments, the tumor cell is a SUP-B15 cell. In some embodiments, the CD19 CAR comprises a scFv antibody fragment. In some embodiments, the scFv antibody fragment has an amino acid sequence of SEQ ID NO: 10. In some embodiments, the multi-cistronic construct comprises a sequence of SEQ ID NO: 9, wherein the sequence encodes the scFv antibody fragment. In some embodiments, the NK-92® cell comprises a sequence encoding a self-cleaving peptide, wherein the sequence is located between the CD19 CAR and CD16, and wherein the sequence allows equimolar expression of the CD19 CAR and the FcR. In some embodiments, the NK-92® cell comprises an internal ribsosomal entry sequence (IRES) between the sequence encoding CD16 and the sequence encoding IL-2 or a variant thereof.

In some embodiments, the direct cytotoxicity of the NK-92® cell on CD19-expressing cells is 70-100% when the effector to target ratio is 10. In some embodiments, the ADCC activity of the NK-92® cell is at 30%-90% when the effector to target ratio is 10. In some embodiments, the CD19 CAR comprises a sequence that shares at least 90% identity to SEQ ID NO: 10.

In some embodiments, this disclosure provides a kit comprising a pharmaceutical composition comprising the NK-92® cell disclosed herein.

In some embodiments, this disclosure provides a method for generating a NK-92® cell comprising providing a vector, wherein the vector encodes a CD19 CAR and a CD16, and introducing the vector into the NK-92® cells to generate the NK-92® cell. In some embodiments, the vector further comprises a sequence that encodes an IL-2. In some embodiments, the vector comprises a sequence encoding a self-cleaving peptide, wherein the sequence is located between CAR and CD16, and wherein the sequence allows equimolar expression of CAR and CD16. In some embodiments, the vector comprises an internal ribosomal entry sequence (IRES) between the CD16 coding sequence and the IL-2 coding sequence.

In some embodiments, this disclosure provides a method of treating a cancer in a subject, comprising administering to the subject a therapeutically effective amount of a composition to the subject, the composition comprising a plurality of the NK-92® cells as claimed. In some embodiments, about $1\times10^8$ to about $1\times10^{11}$ modified cells per $m^2$ of body surface area of the subject are administered to the subject.

In some embodiments, the cancer is a leukemia or a lymphoma.

In some embodiments, the cancer is one or more of B-cell malignancy, B-cell malignancy post-HSCT, CLL, B-ALL, acute lymphoblastic leukemia (ALL), B-lineage lymphoid malignancy post-UCBT, chronic lymphocytic leukemia (CLL), B-Non-Hodgkin's Lymphoma (B-NHL), ALL post-HSCT; lymphoma, refractory follicular lymphoma, or Lymphoblastic leukemia. In some embodiments, the B-cell malignancy is a Mantle cell lymphoma. In some embodiments, the plurality of the NK-92® cells are administered intravenously. In some embodiments, the plurality of the NK-92® cells are administered intratumorally.

The foregoing general description and the following detailed description are exemplary and explanatory and are intended to provide further explanation of the disclosure. Other objects, advantages and novel features will be readily apparent to those skilled in the art.

BRIEF DESCRIPTION OF THE DRAWINGS

The objects, features and advantages will be more readily appreciated upon reference to the following disclosure when considered in conjunction with the accompanying drawings.

FIG. 4A shows cytotoxic effect of CD19 t-haNK™ cells on K562 cells. 16B1 and 18B1 are two CD19 t-haNK™ populations obtained from two electroporation events performed on two different days.

FIG. 6A shows the ADCC activity of the CD19 t-haNK™ cells on SKBr3 cells, when combined with Herceptin (anti-Her2 antibody). The anti CD20 antibody Rituxan was used as a control.

DETAILED DESCRIPTION

Overview

Figure 1:
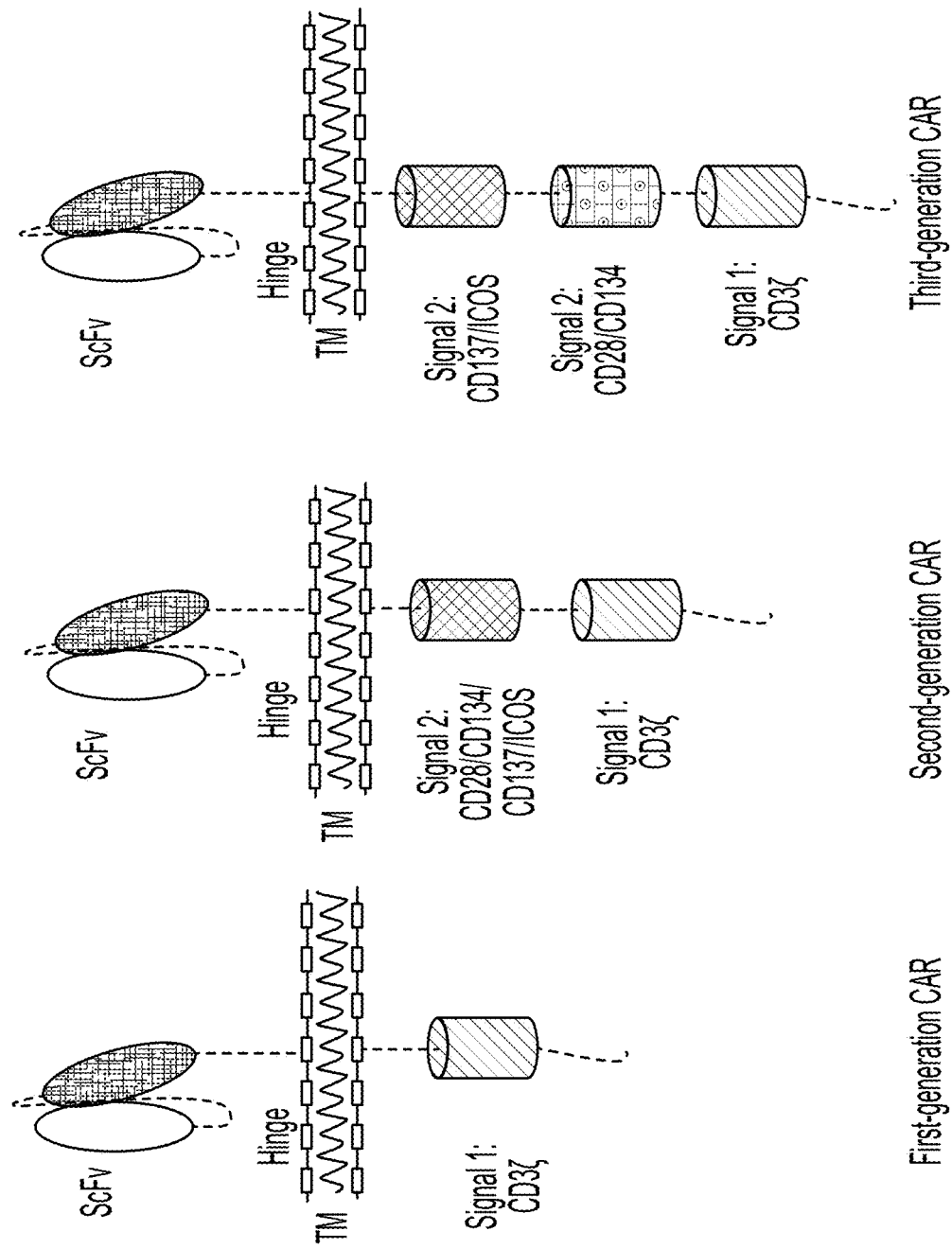
FIG. 1 is a schematic representation of the structure domains of first, second, and third-generation of CARs.

This disclosure provides NK-92® cells that express a CD19 CAR and a Fc receptor. In some embodiments, the cells further express IL-2. In some embodiments, the NK-92® cells comprise a tricistronic construct comprising nucleic acid sequences encoding CD19 CAR and Fc, and an IL2.

Terminology

Unless defined otherwise, all technical and scientific terms used herein have the same meaning as commonly understood by one of ordinary skill in the art.

In this specification and in the claims that follow, reference will be made to a number of terms that shall be defined to have the following meanings:

The terminology used herein is for the purpose of describing particular embodiments only and is not intended to be limiting. As used herein, the singular forms "a," "an" and "the" are intended to include the plural forms as well, unless the context clearly indicates otherwise. Thus, for example, reference to "a natural killer cell" includes a plurality of natural killer cells.

All numerical designations, e.g., pH, temperature, time, concentration, amounts, and molecular weight, including ranges, are approximations which are varied (+) or (−) by increments of 0.1 or 1.0, where appropriate. It is to be understood, although not always explicitly stated, that all numerical designations may be preceded by the term "about."

As used herein, "+", when used to indicate the presence of a particular cellular marker, means that the cellular marker is detectably present in fluorescence activated cell sorting over an isotype control; or is detectable above background in quantitative or semi-quantitative RT-PCR.

As used herein, "−", when used to indicate the presence of a particular cellular marker, means that the cellular marker is not detectably present in fluorescence activated cell sorting over an isotype control; or is not detectable above background in quantitative or semi-quantitative RT-PCR.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

As used herein, the term "substantially the same", used interchangeably with the term "comparable", or "substantially similar", when referring to certain quantifiable properties of the NK-92® cells, such as cytotoxicity, viability or cell doubling time, etc., refers to the that the two measurements of these properties are no more than 15% different, no more than 10%, no more than 8%, or no more than 5% different from each other.

It is also to be understood, although not always explicitly stated, that the reagents described herein are merely exemplary and that equivalents of such are known in the art.

For purposes of this invention and unless indicated otherwise, the term "NK-92®™" is intended to refer to the original NK-92® cell lines as well as NK-92® cell lines, clones of NK-92® cells, and NK-92® cells that have been modified (e.g., by introduction of exogenous genes). NK-92® cells and exemplary and non-limiting modifications thereof are described in U.S. Pat. Nos. 7,618,817; 8,034,332; 8,313,943; 9,181,322; 9,150,636; and published U.S. application Ser. No. 10/008,955, all of which are incorporated herein by reference in their entireties, and include wild type NK-92®, NK-92®-CD16, NK-92®-CD16-γ, NK-92®-CD16-ζ, NK-92®-CD16(F176V), NK-92®MI, and NK-92®CI. NK-92® cells are known to persons of ordinary skill in the art, to whom such cells are readily available from NantKwest®, Inc.

As used herein, the term "NK-92® cells" refers to natural killer cells derived from the highly potent unique cell line described in Gong et al. (Leukemia, April; 8(4): 652-8 (1994)), rights to which are owned by NantKwest® (hereafter, "NK-92® cells").

As used herein, the term "aNK cells" refers to unmodified natural killer cells derived from the highly potent unique cell line described in Gong et al. (Leukemia, April; 8(4): 652-8 (1994)), rights to which are owned by NantKwest® (hereafter, "aNK cells").

As used herein, the term "haNK cells" refers to natural killer cells derived from the highly potent unique cell line described in Gong et al. (Leukemia, April; 8(4): 652-8 (1994)), rights to which are owned by NantKwest®, modified to express CD16 on the cell surface (hereafter, "CD16+ NK-92® cells" or "haNK cells").

As used herein, the term "taNK Cells®" refers to natural killer cells derived from the highly potent unique cell line described in Gong et al. (Leukemia, April; 8(4): 652-8 (1994)), rights to which are owned by NantKwest®, modified to express a chimeric antigen receptor (hereafter, "CAR-modified NK-92® cells" or "taNK Cells®").

As used herein, the term "t-haNK™" cells refers to natural killer cells derived from the highly potent unique cell line described in Gong et al. (Leukemia, April; 8(4): 652-8 (1994)), which are owned by NantKwest®, modified to express CD 16 on the cell surface and to express a chimeric antigen receptor (hereafter, "CAR-modified CD16+ NK-92® cells" or "t-haNK™ cells"). In some embodiments, the tumor specific antigen is CD19, and these NK-92® cells are referred to as CD19 t-haNK™ cells.

As used herein, the term "multi-cistronic construct," refers to a recombinant DNA construct that is to be transcribed into a single mRNA molecule and the single mRNA molecule encodes two or more transgenes. The multi-cistronic construct is referred to as bicistronic construct if it encodes two transgenes, and tricistronic construct if it encodes three genes, and quadro-cistronic construct if it encodes four genes, and so on.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. A CAR-expressing NK-92® cell is targeted to cells expressing certain antigens on the cell surface, based on the specificity of the scFv domain. The scFv domain can be engineered to recognize any antigen, including tumor-specific antigens and virus-specific antigens. For example, CD19 CAR recognizes CD19, a cell surface marker expressed by some cancers.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

As used herein, the term "target," when referring to targeting of a tumor, refers to the ability of NK-92® cells to recognize and kill a tumor cell (i.e., target cell). The term "targeted" in this context refers, for example, to the ability of a CAR expressed by the NK-92® cell to recognize and bind to a cell surface antigen expressed by the tumor.

The term "antibody" refers to an intact immunoglobulin of any isotype, or a fragment thereof that can compete with the intact antibody for specific binding to the target antigen, and includes chimeric, humanized, fully human, and bispecific antibodies. An intact antibody generally comprises at least two full-length heavy chains and two full-length light chains, but in some instances can include fewer chains such as antibodies naturally occurring in camelids which can comprise only heavy chains. Antibodies can be derived solely from a single source, or can be "chimeric," such that different portions of the antibody are derived from two different antibodies. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also includes peptibodies.

The term "subject" refers to a non-human animal, including mammals, such as cats, dogs, cows, horses, pigs, sheep, and goats, and humans. The term subject also refers to a patient in need of treatment for a disease described herein.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claims. "Consisting of" means excluding more than trace amount of other ingredients and substantial method steps. Embodiments defined by each of these transition terms are within the scope of the disclosure.

As used herein, the terms "cytotoxic" and "cytolytic", when used to describe the activity of effector cells such as NK cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK cells is due to cytolysis.

The term "kill" with respect to a cell/cell population is directed to include any type of manipulation that will lead to the death of that cell/cell population.

The term "cytokine" or "cytokines" refers to the general class of biological molecules which effect cells of the immune system. Exemplary cytokines include but are not limited to FLT3 ligand, interferons and interleukins (IL), in particular IL-2, IL-12, IL-15, IL-18 and IL-21.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. The term "administering" or "administration" of a monoclonal antibody or a natural killer cell to a subject includes any route of introducing or delivering the antibody or cells to perform the intended function. Administration can be carried out by any route suitable for the delivery of the cells or monoclonal antibody. Thus, delivery routes can include intravenous, intramuscular, intraperitoneal, or subcutaneous delivery. In some embodiments the modified NK-92® cells are administered directly to the tumor, e.g., by injection into the tumor. In some embodiments the modified NK-92® cells described herein are administered parenterally, e.g., by injection, infusion or implantation (subcutaneous, intravenous, intramuscular, intravesicularly, intratumorally, or intraperitoneal).

The term "expression" refers to the production of a gene product.

As used herein, the term "cytotoxic" when used to describe the activity of effector cells such as NK cells, relates to killing of target cells by any of a variety of biological, biochemical, or biophysical mechanisms.

The terms "decrease," "reduced," "reduction," and "decrease" are all used herein to refer to a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "therapeutically effective amount" or "effective amount" refers to the amount required to ameliorate the symptoms of a disease relative to an untreated patient. The effective amount of active compound(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

Titles or subtitles may be used in the specification for the convenience of a reader, which are not intended to influence the scope of the present disclosure. Additionally, some terms used in this specification are more specifically defined below.

NK-92® Cells

NK-92® is a cytolytic cancer cell line which was discovered in the blood of a subject suffering from a non-Hodgkins lymphoma and then immortalized in vitro. NK-92® cells are derived from NK cells, but lack the major inhibitory receptors that are displayed by normal NK cells, while retaining the majority of the activating receptors. NK-92® cells do not, however, attack normal cells nor do they elicit an unacceptable immune rejection response in humans. Characterization of the NK-92® cell line is disclosed in WO 1998/049268 and U.S. Patent Application Publication No. 2002-0068044. NK-92® cells have been evaluated as a therapeutic agent in the treatment of certain cancers.

Vectors

Described herein are vectors for transfecting cells to produce the modified cells described herein. In one embodiment, the vectors described herein are transient expression vectors. Exogenous transgenes introduced using such vectors are not integrated in the nuclear genome of the cell; therefore, in the absence of vector replication, the foreign transgenes will be degraded or diluted over time.

In one embodiment, the vectors described herein allow for stable transfection of cells. In one embodiment, the vector allows incorporation of the transgene(s) into the genome of the cell. In one embodiment, the vectors have a positive selection marker. Positive selection markers include any genes that allow the cell to grow under conditions that would kill a cell not expressing the gene. Non-limiting examples include antibiotic resistance, e.g. geneticin (Neo gene from Tn5).

In one embodiment, the vector is a plasmid vector. In one embodiment, the vector is a viral vector. As would be understood by one of skill in the art, any suitable vector can be used. Suitable vectors are well-known in the art.

In some embodiments, the cells are transfected with mRNA encoding the protein of interest (e.g., a CAR). Transfection of mRNA results in transient expression of the protein. In one embodiment, transfection of mRNA into NK-92® cells is performed immediately prior to administration of the cells. In one embodiment, "immediately prior" to administration of the cells refers to between about 15 minutes and about 48 hours prior to administration. Preferably, mRNA transfection is performed about 5 hours to about 24 hours prior to administration.

CD19

CD19 is a transmembrane glycoprotein belonging to the immunoglobulin superfamily. It has a single transmembrane domain, a cytoplasmic C-terminus, and an extracellular N-terminus. CD19 is a biomarker for normal and neoplastic B cells, as well as follicular dendritic cells and is critically involved in establishing intrinsic B cell signaling thresholds through modulating both B cell receptor-dependent and independent signaling.

CD19 is expressed in most acute lymphoblastic leukemias (ALL), chronic lymphocytic leukemias (CLL) and B cell lymphomas. The majority of B cell malignancies express CD19 at normal to high levels (80% of ALL, 88% of B cell lymphomas and 100% of B cell leukemias). CD19, though a B cell hallmark, has also been observed in cases of myeloid malignancies, including in 2% of AML cases. Wang et al., Exp. Hematol. Oncol. Nov. 29, 2012; 1:36. Non-limiting examples of malignancies associated with CD19 is shown in Table 1.

TABLE 1

CD19 and Associated Malignancies

| Target antigen | Associated malignancy |
|---|---|
| CD19 | B-cell malignancies |
| | chronic lymphocytic leukemias (CLL) |
| | B- acute lymphoblastic leukemias (ALL) |
| | Acute lymphoblastic leukemias (ALL); ALL post-Hematopoietic stem cell transplantation (HSCT) |
| | Lymphoma; Refractory Follicular Lymphoma; B-NHL |
| | Leukemia |
| | B-cell malignancies; B-cell malignancies post-Hematopoietic stem cell transplantation (HSCT) |
| | B-lineage lymphoid malignancies post-Unrelated Umbilical Cord Blood Transplantation (UCBT) |
| | CLL, B- Non-Hodgkin's Lymphoma (NHL) |
| CD19/CD20 | Lymphoblastic leukemia |

CARs

Phenotypic changes distinguishing a tumor cell from normal cells derived from the same tissue are often associated with one or more changes in the expression of specific gene products, including the loss of normal cell surface components or the gain of others (i.e., antigens not detectable in corresponding normal, non-cancerous tissue). The antigens which are expressed in neoplastic or tumor cells, but not in normal cells, or which are expressed in neoplastic cells at levels substantially above those found in normal cells, have been termed "tumor-specific antigens "or" "tumor-associated antigens." Tumor-specific antigens have been used as targets for cancer immunotherapies. One such therapy utilizes chimeric antigen receptors (CARs) expressed on the surface of immune cells, including T cells and NK cells, to improve cytotoxicity against cancer cells. CARs comprise a single-chain variable fragment (scFv) linked to at least one intracellular signaling domain. The scFv recognizes and binds an antigen on the target cell (e.g., a cancer cell) and triggers effector cell activation. The signaling domains contain immunoreceptor tyrosine-based activation domains (ITAMs) that are important for intracellular signaling by the receptor.

The present disclosure provides NK-92® cells that have been engineered to express at least a chimeric antigen receptor (CAR) on the cell surface. CARs combine an extracellular antigen-recognizing part (usually derived from the variable domain of a specific antibody to an intracellular signaling domain (either single or with additional co-stimulatory elements) that can trigger a cytolytic response once a specific antigen is recognized. There are multiple types of CARs, which all can be used in the application. The first generation of CARs contains one cytoplasmic signaling domain. The signaling domain can be from e.g., the Fc epsilon receptor gamma (FcɛRIγ) which contains one ITAM, or from CD3ζ, which contains three ITAMs. It is believed that CD3ζ CARs are more efficient at tumor eradication than FcɛRIγ CARs. See, e.g., Haynes, et al. 2001, *J. Immunology* 166:182-187; Cartellieri, et al. 2010, *J. Biomed and Biotech*, Vol. 2010, Article ID 956304. The second and third generation CARs combine multiple signaling domains, e.g., the cytoplasmic signaling domain of CD3ζ and costimulatory signaling domains, such as CD28/CD134/CD137/ICOS and CD28/CD134 to a single CAR to promote the activation and proliferation of the NK-92® cells. Thus, in some embodiments, the CD19 CAR expressed by the CD19 t-haNK™ cells comprises a hinge region from CD8, and/or a transmembrane domain of CD28. In some embodiments, the CD19 CAR comprises a cytoplasmic signaling domain of FcɛRIγ. In some embodiments, the CD19 CAR comprises the cytoplasmic signaling domain of CD3ζ. Examples of the hinge region, the transmembrane domain of CD28 and the cytoplasmic signaling domain of FcɛRIγ or CD3ζ are disclosed in U.S. Provisional application No. 62/674,936, the entire content of which is herein incorporated by reference.

While prior publications such as Haynes, et al. 2001, *J. Immunology* 166:182-187 and Cartellieri, et al. 2010, *J. Biomed and Biotech*, Vol. 2010, Article ID 956304, had disclosed that CD3ζ CARs may more efficient at tumor eradication than FcɛRIγ CARs, in this case, the inventors have surprisingly and unexpectedly found that such is not the case for the cells, compositions, and methods disclosed herein. In fact, the inventors found that when the NK-92® cell as disclosed herein has a FcɛRIγ CAR domain, it is just as effective, or in some embodiments even more effective than having a CD3ζ CAR.

Optionally, the CAR is specific for CD19. In some embodiments, CD19 is a human CD19. In some embodiments, the CD19 CAR comprises a scFv fragment comprising the amino acid sequence of SEQ ID NO: 10. In some embodiments, the CD19 CAR comprises the amino acid sequence of SEQ ID NO: 12. In some embodiments the CD19 t-haNK™ cell comprises a nucleic acid sequence of SEQ ID NO: 9, which encodes SEQ ID NO: 10. In some embodiments, the CD19 t-haNK™ cells comprise a nucleic acid sequence of SEQ ID NO: 11, which encodes SEQ ID NO: 12. In some embodiments, the CD19 t-haNK™ cells comprises a tricistronic construct of SEQ ID NO: 13.

In some embodiments, the CD19 CAR polypeptide comprises a sequence that shares at least 90, 91, 92, 93, 94, 95, 96, 97, 98, or 99% identity to SEQ ID NO:10. In some embodiments, an epitope tag peptide, such as FLAG, myc, polyhistidine, or V5 can be added to the amino terminal domain of the polypeptide to assist in cell surface detection by using anti-epitope tag peptide monoclonal or polyclonal antibodies.

In examples, variant polypeptides are made using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce CD16 variants (Ausubel, 2002; Sambrook and Russell, 2001).

In some embodiments, a polynucleotide encoding a CD19 CAR is mutated to alter the amino acid sequence encoding for CAR without altering the function of the CAR. For example, polynucleotide substitutions leading to amino acid substitutions at "non-essential" amino acid residues can be made in SEQ ID NO: 9 or 11.

Conservative substitutions in SEQ ID NO:10 or 12 whereby an amino acid of one class is replaced with another amino acid of the same class, fall within the scope of the disclosed variants as long as the substitution does not materially alter the activity of the polypeptide. Conservative substitutions are well known to one of skill in the art. Non-conservative substitutions that affect (1) the structure of the polypeptide backbone, such as a β-sheet or α-helical conformation, (2) the charge, (3) the hydrophobicity, or (4) the bulk of the side chain of the target site can modify polypeptide function or immunological identity. Non-conservative substitutions entail exchanging a member of one of these classes for another class. Substitutions may be introduced into conservative substitution sites or more preferably into non-conserved sites.

In examples, variant polypeptides are produced using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce variants (Ausubel, 2002; Sambrook and Russell, 2001).

Optionally, the CD19 t-haNK™ cells can be used to treat cancer, in particular, a cancer that express CD19. Optionally, the cancer is selected from the group consisting of leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia), polycythemia vera, lymphomas (e.g., Hodgkin's disease and non-Hodgkin's disease), multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

FC Receptors

In some embodiments, the NK-92® cells are modified to express at least one Fc receptor, such that the at least one Fc receptor is displayed on the cell surface of the NK-92® cell. Fc receptors bind to the Fc portion of antibodies. Several Fc receptors are known, and differ according to their preferred ligand, affinity, expression, and effect following binding to the antibody.

TABLE 2

Illustrative Fc receptors

| Receptor name | Principal antibody ligand | Affinity for ligand | Cell distribution | Effect following binding to antibody |
|---|---|---|---|---|
| FcγRI (CD64) | IgG1 and IgG3 | High (Kd ~$10^{-9}$M) | Macrophages Neutrophils Eosinophils Dendritic cells | Phagocytosis Cell activation Activation of respiratory burst Induction of microbe killing |
| FcγRIIA (CD32) | IgG | Low (Kd >$10^{-7}$M) | Macrophages Neutrophils Eosinophils Platelets Langerhans cells | Phagocytosis Degranulation (eosinophils) |
| FcγRIIB1 (CD32) | IgG | Low (Kd >$10^{-7}$M) | B Cells Mast cells | No phagocytosis Inhibition of cell activity |
| FcγRIIB2 (CD32) | IgG | Low (Kd >$10^{-7}$M) | Macrophages Neutrophils Eosinophils | Phagocytosis Inhibition of cell activity |

TABLE 2-continued

Illustrative Fc receptors

| Receptor name | Principal antibody ligand | Affinity for ligand | Cell distribution | Effect following binding to antibody |
|---|---|---|---|---|
| FcγRIIIA (CD16a) | IgG | Low (Kd >10$^{-6}$M) | NK cells Macrophages (certain tissues) | Induction of antibody-dependent cell-mediated cytotoxicity (ADCC) Induction of cytokine release by macrophages |
| FcγRIIIB (CD16b) | IgG | Low (Kd >10$^{-6}$M) | Eosinophils Macrophages Neutrophils Mast cells Follicular dendritic cells | Induction of microbe killing |
| FcεRI | IgE | High (Kd ~10$^{-10}$M) | Mast cells Eosinophils Basophils Langerhans cells Monocytes | Degranulation Phagocytosis |
| FcεRII (CD23) | IgE | Low (Kd >10$^{-7}$M) | B cells Eosinophils Langerhans cells | Possible adhesion molecule IgE transport across human intestinal epithelium Positive-feedback mechanism to enhance allergic sensitization (B cells) |
| FcαRI (CD89) | IgA | Low (Kd >10$^{-6}$M) | Monocytes Macrophages Neutrophils Eosinophils | Phagocytosis Induction of microbe killing |
| Fcα/μR | IgA and IgM | High for IgM, Mid for IgA | B cells Mesangial cells Macrophages | Endocytosis Induction of microbe killing |
| FcRn | IgG |  | Monocytes Macrophages Dendritic cells Epithelial cells Endothelial cells Hepatocytes | Transfers IgG from a mother to fetus through the placenta Transfers IgG from a mother to infant in milk Protects IgG from degradation |

In some embodiments NK-92® cells are modified to express an Fc receptor protein on the cell surface.

In some embodiments, the Fc receptor is CD16. For purposes of this disclosure, specific amino acid residues of CD16 are designated with reference to SEQ ID NO:2, or to SEQ ID NO:1, which differs at one position relative to SEQ ID NO:1. Thus, an amino acid residue "at position 158" of a CD16 polypeptide is the amino acid residue that corresponds to position 158 of SEQ ID NO:2 (or SEQ ID NO:1), when the CD16 polypeptide and SEQ ID NO:2 are maximally aligned. In some embodiments, NK-92® cells are modified to express a human CD16 that has a phenylalanine at position 158 of the mature form of the protein, e.g., SEQ ID NO:1. In typical embodiments, NK-92® cells are modified to express a high affinity form of human CD16 having a valine at position 158 of the mature form of the protein, e.g., SEQ ID NO:2. Position 158 of the mature protein corresponds to position 176 of the CD16 sequence that includes the native signal peptide. In some embodiments, a CD16 polypeptide is encoded by a polynucleotide that encodes the precursor (i.e., has a native signal peptide) polypeptide sequence of SEQ ID NO:3 or of SEQ ID NO:4. Thus, in one embodiment, the Fc receptor comprises FcγRIII-A (CD16). In some embodiments, the NK-92® cells are genetically modified to express an Fc receptor encoding a polypeptide having at least 90% sequence identity with SEQ ID NO:1 (FcγRIII-A or CD16 having a phenylalanine at position 158 (F-158); or at least 90% identity to SEQ ID NO:2 (CD16 having a valine at position 158 (F158V), higher affinity form).

In some embodiments, a polynucleotide encoding a CD16 polypeptide has at least about 70% polynucleotide sequence identity with a polynucleotide sequence encoding a full-length, including signal peptide, naturally occurring CD16 that has a phenylalanine at position 176 of the full-length CD16 (which corresponds to position 158 of the mature CD16 protein). In some embodiments, a polynucleotide encoding a CD16 polypeptide has at least about 70% polynucleotide sequence identity with a polynucleotide sequence encoding a full-length, including the signal peptide, naturally occurring CD16 that has a valine at position 176 (which corresponds to position 158 of the mature protein). In some embodiments, a polynucleotide encoding CD16 has at least 70%, 80%, 90%, or 95% identity to SEQ ID NO:13 and comprises a codon encoding valine at the position of the polynucleotide that encodes position 176 of the full-length, including the signal peptide, CD16 polypeptide. In some embodiments, a polynucleotide encoding CD16 comprises SEQ ID NO:13, but with a codon encoding valine at position 176 of the full-length CD16.

In some embodiments, the CD16 polynucleotide encodes a polypeptide having at least 70%, 80%, 90%, or 95% identity to SEQ ID NO:1 or SEQ ID NO:2. In some embodiments, the polynucleotide encodes a polypeptide having at least 70% 80%, 90%, or 95% identity to SEQ ID NO:2 and comprises a valine at position 158 as determined with reference to SEQ ID NO:2. In some embodiments the polynucleotide encodes SEQ ID NO:2. In some embodiments, a CD16 polynucleotide encodes an extracellular domain of CD16 with or without the signal sequence, or any other fragment of a full length CD16, or a chimeric receptor encompassing at least partial sequence of CD16 fused to an amino acid sequence of another protein. In other embodiments, an epitope tag peptide, such as FLAG, myc, polyhistidine, or V5 can be added to the amino terminal domain of the mature polypeptide to assist in cell surface detection by using anti-epitope tag peptide monoclonal or polyclonal antibodies.

In some embodiments, homologous CD16 polynucleotides may be about 150 to about 700, about 750, or about 800 polynucleotides in length, although CD16 variants having more than 700 to 800 polynucleotides are within the scope of the disclosure.

Homologous polynucleotide sequences include those that encode polypeptide sequences coding for variants of CD16. Homologous polynucleotide sequences also include naturally occurring allelic variations related to SEQ ID NO:1. Transfection of an NK-92® cell with any polynucleotide encoding a polypeptide having the amino acid sequence shown in either SEQ ID. NO: 1 or SEQ ID NO: 2, a naturally occurring variant thereof, or a sequence that is at least 70% identical, or at least 80%, 90%, or 95% identical to SEQ ID. NO: 1 or SEQ ID NO: 2 is within the scope of the disclosure. In some embodiments, homologous polynucleotide sequences encode conservative amino acid substitutions in SEQ ID. NO: 1 or SEQ ID NO: 2. In some embodiments, NK-92® cells are transfected using a degenerate homologous CD16 polynucleotide sequence that differs from a native polynucleotide sequence, but encodes the same polypeptide.

In other examples, cDNA sequences having polymorphisms that change the CD16 amino acid sequences are used to modify the NK-92® cells, such as, for example, the allelic variations among individuals that exhibit genetic polymorphisms in CD16 genes. In other examples, CD16 genes from other species that have a polynucleotide sequence that differs from the sequence of SEQ ID NO:1 are used to modify NK-92® cells.

Variant polypeptides can be made using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce CD16 variants (Ausubel, 2002; Sambrook and Russell, 2001).

In some embodiments, a polynucleotide encoding a CD16 is mutated to alter the amino acid sequence encoding for CD16 without altering the function of CD16. For example, polynucleotide substitutions leading to amino acid substitutions at "non-essential" amino acid residues can be made in SEQ ID NO:1 or SEQ ID NO:2.

Conservative substitutions in SEQ ID. NO:1 or SEQ ID NO:2, whereby an amino acid of one class is replaced with another amino acid of the same class, fall within the scope of the disclosed CD16 variants as long as the substitution does not materially alter the activity of the polypeptide. Conservative substitutions are well known to one of skill in the art. Non-conservative substitutions that affect (1) the structure of the polypeptide backbone, such as a β-sheet or α-helical conformation, (2) the charge, (3) the hydrophobicity, or (4) the bulk of the side chain of the target site can modify CD16 polypeptide function or immunological identity. Non-conservative substitutions entail exchanging a member of one of these classes for another class. Substitutions may be introduced into conservative substitution sites or more preferably into non-conserved sites.

In some embodiments, CD16 polypeptide variants are at least 200 amino acids in length and have at least 70% amino acid sequence identity, or at least 80%, or at least 90% identity to SEQ ID NO:1 or SEQ ID NO:2. In some embodiments, CD16 polypeptide variants are at least 225 amino acid in length and have at least 70% amino acid sequence identity, or at least 80%, or at least 90% identity to SEQ ID NO:1 or SEQ ID NO:2. In some embodiments, CD16 polypeptide variants have a valine at position 158 as determined with reference to SEQ ID NO:2.

In some embodiments a nucleic acid encoding a CD16 polypeptide may encode a CD16 fusion protein. A CD16 fusion polypeptide includes any portion of CD16 or an entire CD16 fused with a non-CD16 polypeptide. Fusion polypeptides are conveniently created using recombinant methods. For example, a polynucleotide encoding a CD16 polypeptide such as SEQ ID NO:1 or SEQ ID NO:2 is fused in-frame with a non-CD16 encoding polynucleotide (such as a polynucleotide sequence encoding a signal peptide of a heterologous protein). In some embodiment, a fusion polypeptide may be created in which a heterologous polypeptide sequence is fused to the C-terminus of CD16 or is positioned internally in the CD16. Typically, up to about 30% of the CD16 cytoplasmic domain may be replaced. Such modification can enhance expression or enhance cytotoxicity (e.g., ADCC responsiveness). In other examples, chimeric proteins, such as domains from other lymphocyte activating receptors, including but not limited to Ig-a, Ig-B, CD3-e, CD3-d, DAP-12 and DAP-10, replace a portion of the CD16 cytoplasmic domain.

Fusion genes can be synthesized by conventional techniques, including automated DNA synthesizers and PCR amplification using anchor primers that give rise to complementary overhangs between two consecutive gene fragments that can subsequently be annealed and reamplified to generate a chimeric gene sequence (Ausubel, 2002). Many vectors are commercially available that facilitate sub-cloning CD16 in-frame to a fusion moiety.

Cytokines

The cytotoxicity of NK-92® cells is dependent on the presence of cytokines (e.g., interleukin-2 (IL-2)). The cost of using exogenously added IL-2 needed to maintain and expand NK-92® cells in commercial scale culture is significant. The administration of IL-2 to human subjects in sufficient quantity to continue activation of NK92 cells would cause adverse side effects.

In one embodiment, NK-92® cells are modified to express at least one cytokine. In particular, the at least one cytokine is IL-2 (SEQ ID NO:6), IL-12, IL-15, IL-18, IL-21, or a variant thereof. In some embodiments, the cytokine is IL-2, IL-15, or a variant thereof. In certain embodiments, the IL-2 is a variant that is targeted to the endoplasmic reticulum, and the the IL-15 is a variant that is targeted to the endoplasmic reticulum.

In one embodiment, the IL-2 is cloned and expressed with a signal sequence that directs the IL-2 to the endoplasmic reticulum (erIL-2) (SEQ ID NO: 7). This permits expression of IL-2 at levels sufficient for autocrine activation, but without releasing IL-2 extracellularly. See Konstantinidis et al "Targeting IL-2 to the endoplasmic reticulum confines autocrine growth stimulation to NK-92® cells" *Exp Hema-*

*tol.* 2005 February; 33(2):159-64. Continuous activation of the FcR-expressing NK-92® cells can be prevented, e.g., by the presence of the suicide gene.

Suicide Gene

The term "suicide gene" refers to a transgene that allows for the negative selection of cells expressing the suicide gene. A suicide gene is used as a safety system, allowing cells expressing the gene to be killed by introduction of a selective agent. This is desirable in case the recombinant gene causes a mutation leading to uncontrolled cell growth, or the cells themselves are capable of such growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene. Typically, the suicide gene encodes for a protein that has no ill effect on the cell but, in the presence of a specific compound, will kill the cell. Thus, the suicide gene is typically part of a system.

In one embodiment, the suicide gene is active in NK-92® cells. In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

In another embodiment, the suicide gene is cytosine deaminase, which is toxic to cells in the presence of 5-fluorocytosine. Garcia-Sanchez et al. "Cytosine deaminase adenoviral vector and 5-fluorocytosine selectively reduce breast cancer cells 1 million-fold when they contaminate hematopoietic cells: a potential purging method for autologous transplantation." *Blood.* 1998 Jul. 15; 92(2):672-82.

In another embodiment, the suicide gene is cytochrome P450, which is toxic in the presence of ifosfamide or cyclophosphamide. See, e.g. Touati et al. "A suicide gene therapy combining the improvement of cyclophosphamide tumor cytotoxicity and the development of an anti-tumor immune response." *Curr Gene Ther.* 2014; 14(3):236-46.

In another embodiment, the suicide gene is iCasp9. Di Stasi, (2011) "Inducible apoptosis as a safety switch for adoptive cell therapy." *N Engl J Med* 365: 1673-1683. See also Morgan, "Live and Let Die: A New Suicide Gene Therapy Moves to the Clinic" Molecular Therapy (2012); 20: 11-13. iCasp9 induces apoptosis in the presence of a small molecule, AP1903. AP1903 is biologically inert small molecule, that has been shown in clinical studies to be well tolerated, and has been used in the context of adoptive cell therapy.

Codon Optimization

In some embodiments, the sequence of the constructs used to transform the aNK cells are codon-optimized to maximize expression efficiency of CD19 CAR, CD16, and/or erIL-2 in human systems. Codon optimization is typically performed by modifying a nucleic acid sequence by replacing at least one, more than one, or a significant number of codons in the native sequence with codons that are more frequently or most frequently used in the gene of the expression system. Codon optimization can be used to the rate of translation or to produce recombinant RNA transcripts having desirable properties, such as a longer half-life, as compared with transcripts produced using a non-optimized sequence. Methods for codon optimization are readily available, for example, GeneArt™, from Thermo Fisher Scientific (Waltham, MA); Optimizer, accessible free of charge at http://genomes.urv.es/OPTIMIZER, and GeneGPS Expression Optimization Technology from DNA 2.0 (Newark, California). In particular embodiments, the coding sequence for CD19 CAR is codon-optimized and comprises the sequence as set forth in SEQ ID NO: 9.

Transgene Expression

Transgenes can be engineered into an expression vector by any mechanism known to those of skill in the art. Where multiple transgenes are to be inserted into a cell, transgenes may be engineered into the same expression vector or a different expression vector.

In some embodiments, the cells are transfected with mRNA encoding the transgenic protein to be expressed.

Transgenes and mRNA can be introduced into the NK-92® cells using any transfection method known in the art, including, by way of non-limiting example, infection, electroporation, lipofection, nucleofection, or "gene-gun."

NK-92® Cells that Express a CD19 CAR

This disclosure provides a modified NK-92® cell expressing a CD19 CAR and a FcR. Optionally, the modified NK-92® cell further expresses an IL-2.

In some embodiments, the modified NK-92® cells comprise a multi-cistronic transgene and the multi-cistronic transgene encodes the chimeric antigen receptor and the Fc receptor, and optionally IL-2.

In some embodiments, the FcR is a CD16. In some embodiments, the CD16 is a high affinity CD16, which comprises or consists of SEQ ID NO:2. In some embodiments the IL-2 is erIL-2, which comprises or consists of SEQ ID NO: 7.

In some embodiments, the CD19 CAR-coding sequence and the CD16-coding sequence are separated by a sequence encoding a self-cleaving peptide in order to produce equimolar expression levels of CD19 CAR and CD16 encoded from the same mRNA. Self-cleaving peptides and their coding sequences are well known, for example, as disclosed in Wang et al., Scientific Reports 5, Article number 16273 (2015), the relevant disclosure of which is herein incorporated by reference. Non-limiting examples of the self-cleaving peptides include the porcine teschovirus-1 2A (P2A), thosea asigna virus 2A (T2A), equine rhinitis A virus 2A (E2A), cytoplasmic polyhedrosis virus (BmCPV 2A), and flacherie virus (BmIFV 2A) of B. mori. In some embodiments, the self-cleaving peptide is a P2A peptide encoded by SEQ ID NO: 8: ggaageggagctactaacttcagcctgctgaagcaggctggagacgtggaggagaaccctggacct.

In some embodiments, the CD16 coding sequence and the erIL-2-coding sequence are separated by an internal ribosomal entry sequence (IRES) that allows for initiation of translation from an internal region of an mRNA transcribed from the nucleic acid sequences.

Figure 2:
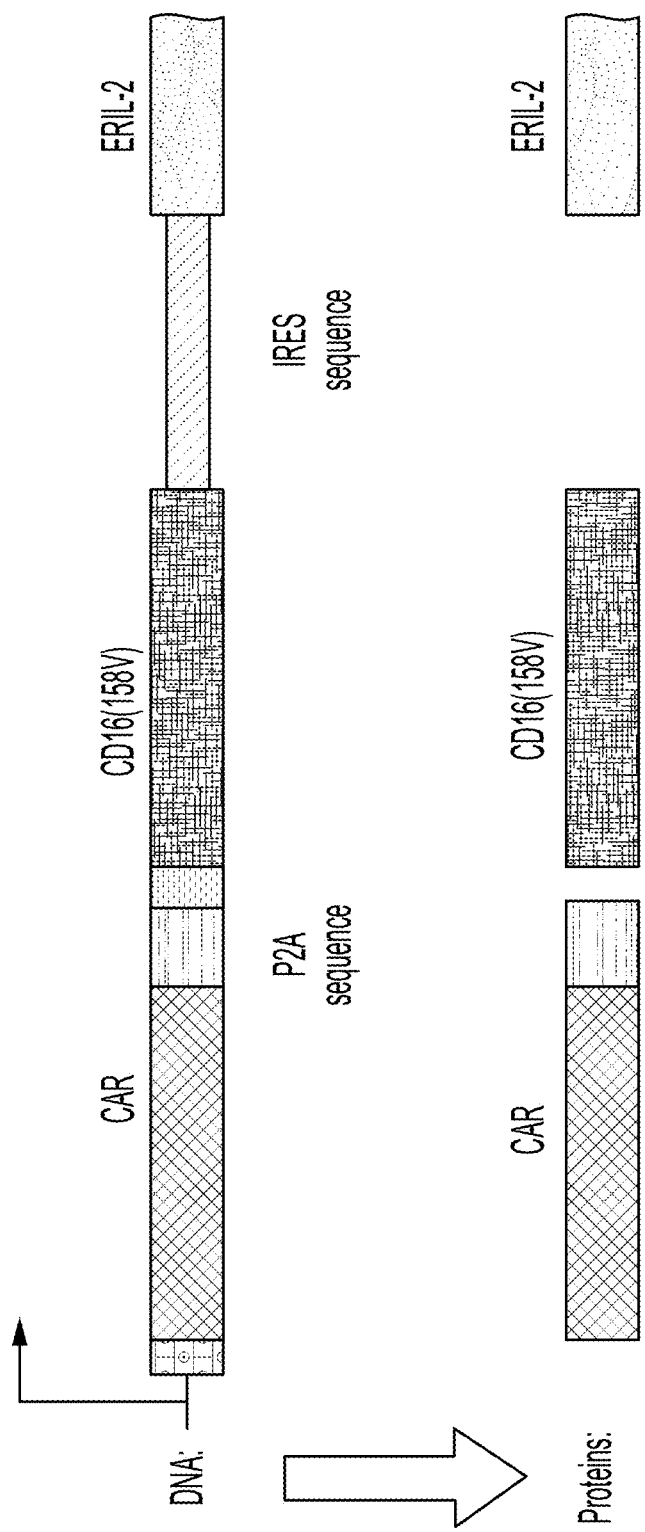
FIG. 2 shows the components of a tricistronic plasmid comprising a CAR coding sequence, a P2A sequence, a CD16 coding sequence, and an erIL-2 coding sequence.

In some embodiments, the NK-92® cells comprise a tricistronic construct which expresses a CAR, a high affinity CD16, and an erIL-2 from a single mRNA. The integration of the CAR enables effector cells to specifically engage and kill target cells that express a target recognized by the CAR; the integration of CD16 enables ADCC when combined with a therapeutic monoclonal antibody; and erIL2, which allows cell expansion in absence of exogenous IL-2 and maintains selective pressure for transgene expression. One illustrative tricistronic construct is shown in FIG. 2.

To produce modified NK-92® cells expressing a CAR and a CD16 (e.g., the high affinity CD16), and an erIL-2, the multi-cistronic plasmid is introduced into the aNK cells by, for example, electroporation. The transformed NK-92® cells are grown in media free of IL-2, and individual clones can be selected from the transformed NK-92® cells by limiting dilution cloning and characterized based on criteria, which include, for example, high levels of CAR and CD16 expression, cytotoxicity, ADCC, growth rate, and/or IL-2 secretion. Suitable clones may also express surface markers, e.g., CD3, CD16, CD54, CD56, NKG2D, and/or NKp30 in levels substantially similar to that of the aNK cells. Optionally, whole genome sequencing (WGS) are performed to determine the transgene integration site. Clones meeting one or more of these criteria can be selected for further development and used to treat patients in clinic.

Expression

Expression of IL-2 can be confirmed by the capability of the modified NK-92® cells in IL-2 free conditions. Expression of the CAR and CD16 can be measured by flow cytometry. For NK-92® cells that have been transformed with the tricistronic construct comprising the coding sequences of CD19 CAR, CD16, and IL-2 (e.g., erIL-2), typically at least 70%, at least 80%, at least 85% of the transformed cells that are able to grow IL-2-free conditions also show high expression levels of both CAR and CD16.

Optionally, IL-2 secretion levels of the transformed NK-92® cells can be measured at various time points using methods well known in the art, for example, by ELISA.

In some embodiments, the IL-2 levels in the culture supernatant are measured to determine the levels of IL-2 released to the cell culture medium. In some embodiments, the IL-2 levels in the cell pellets are measured to assess total intracellular levels of IL-2. In some embodiments, both the IL-2 amount in the supernatant and the IL-2 amount in the cell pellets are measured to determine the total amount of IL-2 produced by the transformed NK-92® cells.

Optionally, other surface markers of the transformed NK-92® cells can be measured by flow cytometry. These markers include, but are not limited to, CD54, CD56, NKG2D, NKp30, and CD3. Suitable clones are those that have demonstrated substantially similar expression levels of these markers to those of aNK cells under the same growth conditions.

Cytotoxicity

Optionally, the cytotoxicity of the NK-92® cells transformed with the tricistronic plasmid can be assessed using a flow-based in cytotoxicity assay. Effector cells (the NK-92® cells) and fluorophore-labeled target cells, e.g., tumor cells, are mixed at different effector to target ratios. Propidium Iodide (PI) can be added to the cells and samples can be analyzed a flow cytometer. Preferably the fluorophore that is used to label the target cells can be distinguished from PI by in a flow cytometer. In some embodiments, the fluorophore is CF SE. In some embodiments, the fluorophore is PKHGL67. The cytotoxicity can be determined by the % of PI-positive cells within the fluorophore-positive target population.

Optionally, cytotoxicity of the NK-92® cells transformed with the tricistronic plasmid can also be tested using methods well known in the art. Cytotoxicity of NK-92® cells can be reflected by their direct cytotoxicity or ADCC activity. Direct cytotoxicity of the produced NK-92® cells, the ability to target and kill aberrant cells, such as tumor cells, can be assessed by methods well known in the art, for example, a $^{51}$Cr release assay (Gong et al. (Leukemia, April; 8(4): 652-8 (1994)) using the procedure described by Klingemann et al. (Cancer Immunol. Immunother. 33:395-397 (1991)). In some embodiments, the target cells express an antigen that can be recognized by the CAR expressed on the surface of the t-haNK™ cells. Briefly, $^{51}$Cr-labeled target cells are mixed with NK-92® cells and are lysed. The percentage of specific cytotoxicity can be calculated based on the amount of released $^{51}$Cr. See Patent Pub. No. US20020068044.

Alternatively, direct cytotoxicity of the produced NK-92® cells can also be assessed using a calcein release assay. For example, the NK-92® cells (referred to as the effector in the assay) can be mixed with the calcein loaded target cells (referred to as target in the assay) at certain ratios. After incubation for a period of time, the calcein released from the target cells can be assessed, e.g., by a fluorescence plate reader.

The ratio of the effector and target used in each of the assays may vary, optionally the effector:target ratio may be 20:1, 15:1, 10:1, 8:1, or 5:1; preferably the effector:target ratio is 10:1. The target cells can be any cells that express an antigen molecule that can be recognized by the CAR on the NK-92® cells (t-haNK™ cells). For example, SUP-B15 cells can be recognized by the CD19 CAR and are target cells for CD19 t-haNK™ cells. The values of cytotoxicity of NK-92® cells may vary depending on the type of target cells used as well as the effector:target ratio. In general, the NK-92® cells produced using the methods described herein can have a cytotoxicity of 60-100%, e.g., 70-100% or 80-100%. In some cases, the NK-92® cells may have a cytotoxicity of 80-100%, e.g., 82-100%, 85-100%, 87-100%, 88-100%, or 89-100%, by a calcein release assay when using an effector:target ratio of 1:1.

Optionally, the cytotoxicity of NK-92® cells, e.g., t-haNK™ cells, that is assessed is the antibody dependent cytotoxicity (ADCC). Methods for measuring the ADCC activity of NK-92® cells are similar to the methods of measuring direct cytotoxicity as described above except that an antibody that can recognize the target cell is also added. The Fc receptor of the NK cells recognizes the cell-bound antibodies and triggers cytolytic reaction and killing the target cells. In one illustrative example, the t-haNK™ cells can be incubated with Herceptin (an anti-Her2 antibody) and SKBr3 (target cells) and killing of the SKBr3 cells can be measured by the release of internal components of the target cells, e.g., $^{51}$Cr or calcein, as described above, or by the PI staining of the target cells.

Doubling Time

The growth rate of the NK-92® cells, e.g., t-haNK™ cells, can be assessed using cell doubling time, i.e., the time it takes for the cells to proliferate to reach twice the initial cell number. The doubling time is reversely related to the growth rate of the NK-92® cells; the greater the doubling time, the lower the growth rate.

WGS

Optionally, whole genome sequencing (WGS) of the transformed NK-92® cells are performed to identify the insertion site of the multi-cistronic construct.

Therapeutic Applications

This disclosure also provides a method to treat any type of cancer in a subject at any stage of the disease. Non-limiting examples of the suitable cancers include carcinoma, melanoma, or sarcoma. In some embodiments, the invention is used to treat cancer of hemopoietic origin such as leukemia or lymphoma. In some embodiments, the cancer is a solid tumor.

In some embodiments, the method to treat any type of cancer in a subject comprises administering to the patient a therapeutically effective amount of the NK-92® cells as described above, wherein the thereby treating cancer. In some embodiments, the NK-92® cells express a Fc receptor, e.g., a high affinity Fc receptor that has the sequence set forth in SEQ ID NO:2. In some embodiments, the NK-92® cells express a CD19 CAR, a Fc receptor and an IL-2. In some embodiments, the modified NK-92® cells comprise a multi-cistronic construct and wherein the multi-cistronic construct encodes the chimeric antigen receptor and the Fc receptor.

Also provided are methods of treating a subject in need thereof with the modified NK-92® cells as described herein. In some embodiments, the subject or patient is suffering from cancer or an infectious disease, such as a viral infection.

The modified NK-92® cells can be administered to an individual by absolute numbers of cells, e.g., said individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) NK-92® cells per injection, or any ranges between any two of the numbers, end points inclusive. Therefore, this disclosure also provides a composition comprising a plurality of NK-92® cells, wherein the number of cells are $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, or $5\times10^3$ (and so forth).

In other embodiments, said individual can be administered from about 1000 cells/injection/$m^2$ to up to about 10 billion cells/injection/$m^2$, such as at about, at least about, or at most about, $1\times10^8/m^2$, $1\times10^7/m^2$, $5\times10^7/m^2$, $1\times10^6/m^2$, $5\times10^6/m^2$, $1\times10^5/m^2$, $5\times10^5/m^2$, $1\times10^4/m^2$, $5\times10^4/m^2$, $1\times10^3/m^2$, $5\times10^3/m^2$ (and so forth) NK-92® cells per injection, or any ranges between any two of the numbers, end points inclusive.

In other embodiments, NK-92® cells can be administered to such individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, or $5\times10^3$ (and so forth) NK-92® cells per kilogram of the individual, or any ranges between any two of the numbers, end points inclusive.

In other embodiments, the total dose may be calculated by $m^2$ of body surface area, including about $1\times10^{11}$, $1\times10^{10}$, $1\times10^9$, $1\times10^8$, $1\times10^7$, per $m^2$, or any ranges between any two of the numbers, end points inclusive. The average person is about 1.6 to about 1.8 $m^2$. In a preferred embodiment, between about 1 billion and about 3 billion NK-92® cells are administered to a patient. In other embodiments, the amount of NK-92® cells injected per dose may calculated by $m^2$ of body surface area, including $1\times10^{11}$, $1\times10^{10}$, $1\times10^9$, $1\times10^8$, $1\times10^7$, per $m^2$. The average body surface area for a person is 1.6-1.8 $m^2$.

In other embodiments, NK-92® cells can be administered to such individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, or $5\times10^3$ (and so forth) NK-92® cells per kilogram of the individual, or any ranges between any two of the numbers, end points inclusive.

NK-92® cells can be administered once to a patient with cancer or they can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In some embodiments, NK-92® cells are administered in a composition comprising the NK-92® cells and a medium, such as human serum or an equivalent thereof. In some embodiments, the medium comprises human serum albumin. In some embodiments, the medium comprises human plasma. In some embodiments, the medium comprises about 1% to about 15% human serum or human serum equivalent. In some embodiments, the medium comprises about 1% to about 10% human serum or human serum equivalent. In some embodiments, the medium comprises about 1% to about 5% human serum or human serum equivalent. In a preferred embodiment, the medium comprises about 2.5% human serum or human serum equivalent. In some embodiments, the serum is human AB serum. In some embodiments, a serum substitute that is acceptable for use in human therapeutics is used instead of human serum. Such serum substitutes may be known in the art, or developed in the future. Although concentrations of human serum over 15% can be used, it is contemplated that concentrations greater than about 5% will be cost-prohibitive. In some embodiments, NK-92® cells are administered in a composition comprising NK-92® cells and an isotonic liquid solution that supports cell viability. In some embodiments, NK-92® cells are administered in a composition that has been reconstituted from a cryopreserved sample.

Pharmaceutically acceptable compositions comprising the NK-92® cells can include a variety of carriers and excipients. A variety of aqueous carriers can be used, e.g., buffered saline and the like. These solutions are sterile and generally free of undesirable matter. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. As used herein, the term pharmaceutically acceptable is used synonymously with physiologically acceptable and pharmacologically acceptable. A pharmaceutical composition will generally comprise agents for buffering and preservation in storage and can include buffers and carriers for appropriate delivery, depending on the route of administration.

These compositions for use in in vivo or in vitro may be sterilized by sterilization techniques employed for cells. The compositions may contain acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of cells in these formulations and/or other agents can vary and will be selected primarily based on fluid volumes, viscosities, body weight and the like in accordance with the particular mode of administration selected and the subject's needs.

In one embodiment, NK-92® cells are administered to the patient in conjunction with one or more other treatments or agent for the cancer being treated. In some embodiments, the one or more other treatments for the cancer being treated include, for example, an antibody, radiation, chemotherapeutic, stem cell transplantation, or hormone therapy.

In some embodiments, NK-92® cells and the other cancer agent/treatment are administered simultaneously or approximately simultaneously (e.g., within about 1, 5, 10, 15, 20, or 30 minutes of each other). In some embodiments, the NK-92® cells and the other cancer agent/treatment are administered sequentially. In some embodiments, the other cancer treatment/agent is administered one, two, or three days after the administration of the NK-92® cells.

In one embodiment, the other cancer agent is an antibody. In one embodiment, NK-92® cells are administered in conjunction with an antibody targeting the diseased cells. In one embodiment, NK-92® cells and an antibody are administered to the patient together, e.g., in the same formulation; separately, e.g., in separate formulations, concurrently; or can be administered separately, e.g., on different dosing schedules or at different times of the day. When administered separately, the antibody can be administered via any suitable route, such as intravenous or intra-tumoral injection.

In some embodiments, NK-92® cells of the present disclosure are used in combination with therapeutic antibodies and/or other anti-cancer agents. Therapeutic antibodies may be used to target cells that express cancer-associated or tumor-associated markers. Examples of cancer therapeutic monoclonal antibodies are shown in Table 4. In some embodiments, the NK-92® cells express a Fc receptor, e.g., a high affinity Fc receptor that has the sequence set forth in SEQ ID NO:2. In some embodiments, the NK-92® cells are haNK® cells. In one embodiment, the therapeutic antibody is avelumab.

TABLE 3

Illustrative therapeutic monoclonal antibodies
Examples of FDA-approved therapeutic monoclonal antibodies

| Antibody | Brand name | Company | Target | Indication (Targeted disease) |
|---|---|---|---|---|
| Alemtuzumab | Campath ® | Genzyme | CD52 | Chronic lymphocytic leukemia |
| Brentuximab vedotin | Adcetris ® | | CD30 | Anaplastic large cell lymphoma (ALCL) and Hodgkin lymphoma |
| Cetuximab | Erbitux ® | Bristol-Myers Squibb/Eli Lilly/Merck KGaA | epidermal growth factor receptor | Colorectal cancer, Head and neck cancer |
| Gemtuzumab | Mylotarg ® | Wyeth | CD33 | Acute myelogenous leukemia (with calicheamicin) |
| Ibritumomab tiuxetan | Zevalin ® | Spectrum Pharmaceuticals, Inc. | CD20 | Non-Hodgkin lymphoma (with yttrium-90 or indium-111) |
| Ipilimumab (MDX-101) | Yervoy ® | | blocks CTLA-4 | Melanoma |
| Ofatumumab | Arzerra ® | | CD20 | Chronic lymphocytic leukemia |
| Palivizumab | Synagis ® | MedImmune | an epitope of the RSVF protein | Respiratory Syncytial Virus |
| Panitumumab | Vectibix ® | Amgen | epidermal growth factor receptor | Colorectal cancer |
| Rituximab | Rituxan ®, Mabthera ® | Biogen Idec/Genentech | CD20 | Non-Hodgkin lymphoma |
| Tositumomab | Bexxar ® | GlaxoSmithKline | CD20 | Non-Hodgkin lymphoma |
| Trastuzumab | Herceptin ® | Genentech | ErbB2 | Breast cancer |
| Blinatunomab | | | bispecific CD19-directed CD3 T-cell engager | Philadelphia chromosome-negative relapsed or refractory B cell precursor acute lymphoblastic leukemia (ALL) |
| Avelumab | Bavencio ® | Merck KGaA and Pfizer and Eli Lilly | anti-CD19 | Non-small cell lung cancer, metastatic Merkel cell carcinoma; gastic cancer, breast cancer, ovarian cancer, bladder cancer, melanoma, meothelioma, including metastatic or locally advanced solid tumors |
| Daratumumab | | | CD38 | Multiple myeloma |
| Elotuzumab | | | a SLAMF7-directed (also known as CD319) immunostimulatory antibody | Multiple myeloma |

Administration of such NK-92® cells may be carried out simultaneously with the administration of the monoclonal antibody, or in a sequential manner. In some embodiments, the NK-92® cells are administered to the subject after the subject has been treated with the monoclonal antibody. Alternatively, the NK-92® cells may be administered at the same time, e.g., within 24 hours, of the monoclonal antibody.

In some embodiments, NK-92® cells are administered intravenously. In some embodiments the NK-92® cells are infused directly into the bone marrow.

Therefore, this disclosure provides a method of treating cancer or viral infection in a patient in need thereof, the method comprising administering to the patient a therapeutically effective amount of the NK-92® cells disclosed herein to thereby treating cancer.

Kits

Also disclosed are kits for the treatment of cancer or an infectious disease using compositions comprising a plurality of NK-92® cells as described herein. In some embodiments, the kits of the present disclosure may also include at least one monoclonal antibody. The NK-92® cell included in the kit expresses a CAR and a Fc receptor. In some embodiments, the NK-92® cell further expresses an IL-2, e.g., an erIL-2 or an IL-15, e.g., an erIL-15. In some embodiments, the NK-92® cell comprises a multi-cistronic construct and wherein the multi-cistronic construct encodes the chimeric antigen receptor, the Fc receptor, and optionally IL-2 or IL-15.

In certain embodiments, the kit may contain additional compounds such as therapeutically active compounds or drugs that are to be administered before, at the same time or after administration of NK-92® cells. Examples of such compounds include an antibody, vitamins, minerals, fludrocortisone, ibuprofen, lidocaine, quinidine, chemotherapeutic, etc.

In various embodiments, instructions for use of the kits will include directions to use the kit components in the treatment of a cancer or an infectious disease. The instructions may further contain information regarding how to handle the NK-92® cells (e.g., thawing and/or culturing). The instructions may further include guidance regarding the dosage and frequency of administration.

In certain embodiments, the kit further comprises one or more containers filled with one or more compositions described herein, e.g., a composition comprising NK-92® cells as described herein. Optionally associated with such containers can be a label indicating the kit is for treating a cancer, such as those described herein. Optionally the label also includes a notice in the form prescribed by a governmental agency regulating the manufacture, use or sale of pharmaceuticals or biological products, which notice reflects approval by the agency of manufacture, use or sale for human administration.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

EXAMPLES

The following examples are for illustrative purposes only and should not be interpreted as limitations. There are a variety of alternative techniques and procedures available to those of skill in the art which would similarly permit one to successfully perform the examples below.

Example 1: Producing the CD19 CAR Modified NK-92® Cells

CD19 CAR was cloned into a tricistronic plasmid pNEUKv1 FcR_IL-2 vector that also contains CD16 and erIL-2 transgenes. The tricistronic plasmids were electroporated into the aNK cells. The CD19 CAR-expressing NK-92® cells were selected by IL-2-depleted media because untransformed aNK cells, being IL-2 dependent, could not survive in IL-2 depleted media.

Limiting Dilution Cloning

An aliquot of a polyclonal CD19 t-haNK™ pool culture diluted to a density of 3 cells/ml in growth medium without IL-2 supplementation. This cell suspension was aliquoted in 96-well plates at a volume of 200 µl per well, corresponding to 0.6 cells per well on average. The plates were incubated at 37° C. for 10 days, then visually checked for cell growth. A total of 20 cultures, now named clones, were picked and transferred to larger vessels and were numbered according to their initial growth speed, with clones #1 to 10 being first to be passaged.

Example 2. Bioanalytical Methods

Cell Culture

Polyclonal and clonal CD19 t-haNK™ cells were culture in growth medium supplemented with 5% heat inactivated human AB serum (from CMV-negative tested donors), without IL-2.

aNK cells were cultured in growth medium supplemented with 5% heat inactivated human AB serum (from CMV-negative tested donors) and 500 IU/ml recombinant human IL-2.

haNK cells were cultured in growth medium supplemented with 5% heat inactivated human AB serum (from CMV-negative tested donors), without IL-2.

K562 cells were cultured in RPMI-1640 supplemented with 10% heat inactivated fetal bovine serum and a cocktail of antibiotics/antimycotic. K562 cells were passaged every 2-5 days, or whenever the culture medium appeared yellow.

SUP-B15 and SUP-B15$^{CD19KO/CD20+}$ cells were cultured in RPMI-1640 supplemented with 20% heat inactivated fetal bovine serum, 55 uM of beta-mercaptoethanol, and a cocktail of antibiotics/antimycotic. Cells were otherwise passaged as K562 cells above.

Antibody Staining for Flow Cytometry Analysis

Cells were harvested by centrifugation, washed twice in FACS buffer (5% FBS in 1×D-PBS), and resuspended in 1 ml FACS buffer. For direct fluorophore-conjugated antibody staining of surface proteins, cells were incubated with an appropriate conjugated antibody (or isotype control) for 20 mins at 4° C. in the dark, then washed twice with FACS buffer. For detection of CAR proteins, cells were incubated with Biotinylated Anti F(ab')$_2$ Fragment antibody, followed by incubation with Streptavidin-APC antibody. Samples were analyzed on a MACSQuant Flow cytometer.

Growth Assay

From an initial concentration of 1×10$^5$ cell/mL resuspended in growth medium supplemented with 5% heat inactivated human AB serum (on Day 1), cultures were counted on Day 3, Day 5, and Day 7 by automated cell counter. Growth rates were calculated by the following formula:

Doubling time(hrs)=[Duration(hrs)×log(2)]/[log(final cell density)−log(initial cell density)]

Cytotoxicity

Suspension-growing cell lines were resuspended by up and down pipetting of the cell cultures. Cells viability was determined by automated counting (trypan blue exclusion method). Target cells were labelled with CFSE dye, and dilutions of target and effector cells to the required cell concentrations were made in RPMI-1640 supplemented with 10% heat-inactivated FBS and antibiotics/antimycotic. Effector and target cells were mixed at different effector to target (E:T of 20:1, 10:1, 5:1, 2.5:1, 1.25:1, 0.62:1, 0.31:1, and 0.15:1) ratios in a 96-well plate and co-incubated for 4 h in a 5% CO2 atmosphere 37° C. incubator. PI was then added for fluorescent labelling of dead cells and the assay was analyzed on a MACSquant flow cytometry device.

ADCC

Suspension-growing cell lines were resuspended by up and down pipetting of the cell cultures. Cells viability was determined by automated counting (trypan blue exclusion method). Target cells were labelled with PKH67-GL dye, and dilutions of target and effector cells to the required cell concentrations were made in RPMI-1640 supplemented with 10% heat-inactivated FBS and antibiotics/antimycotic. Target cells were pre-incubated with monoclonal antibodies trastuzumab, rituximab, or no antibody for 30 min at R.T. Antibody-labelled target cells (and no-antibody controls) were then mixed with effector cells at different effector to target ratios (E:T of 20:1, 10:1, 5:1, 2.5:1, 1.25:1, 0.62:1, 0.31:1, and 0.15:1) in a 96-well plate and co-incubated for 4 h in a 5% CO$_2$ atmosphere 37° C. incubator. PI was then added for fluorescent labelling of dead cells and the assay was analyzed on a MACSquant flow cytometry device.

Quantification of IL-2

Cells for analysis were washed in D-PBS 1× to remove leftover medium, resuspended in fresh growth medium and aliquoted in triplicate in two 96-well plates each at a density of 10$^5$ cells/well (=200 μl/well) and the plates were incubated at 37° C. in a 5% CO$_2$ humidified incubator. One set of plates was taken for analysis after 24 h of incubation, the other one was taken at 48 h. Sample supernatants for analysis were prepared by a first centrifugation step at 500×g for 5 min to remove cells, followed by a second centrifugation at 2000×g for 5 min to remove cell debris. Sample supernatants were frozen at −80° C. until analysis. Cell pellets from the 500×g centrifugation step were resuspended, triplicates were pooled and the cell density was recorded. The concentration of IL-2 in the sample supernatants was measured using a human IL-2 ELISA detection kit, available from ThermoFisher Scientific (Waltham, MA), according to the manufacturer's instructions and compared to a provided standard. IL-2 concentrations were normalized to cell numbers at 24 and 48 h and expressed as pg/ml/10$^5$ cells.

Example 3: Phenotypes of the Modified NK-92® Cells

Figure 3A:
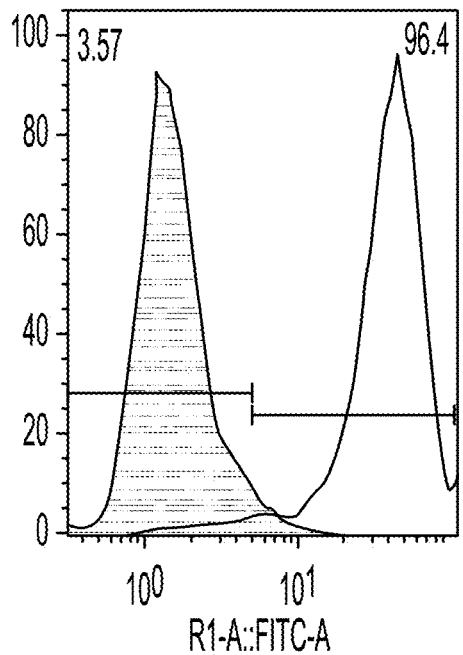
FIGS. 3A and 3B show the results of flow cytometric analysis, showing the expression of CD16 and CD19-CAR on the surface of CD19 t-haNK™ cells. The peak on the right of each plot represent the population of cells expressing CD16 or CD19.
Figure 3B:
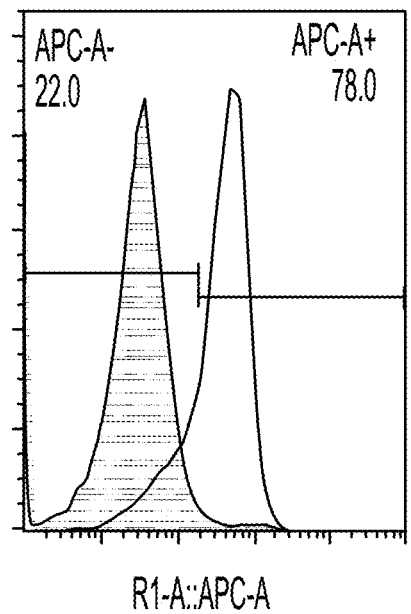

Expression of CD19 CAR in CD19 t-haNK™ cells were measured by flow cytometry and the results showed that the CD19 t-haNK™ cells were able to grow in absence of IL-2 and more than 80% of the cells express a high level of both CD16 (FIG. 3A) and CAR (FIG. 3B).

In a separate experiment, twenty selected clones were screened for surface expression of CD19CAR (detected by biotinylated F(ab')$_2$ fragment specific primary antibody and streptavidin-APC secondary antibody) and CD16 (detected by 3G8 monoclonal antibody) by flow cytometry. Clones that displayed multiple positive populations, low staining intensity for CD16, or high background were discarded.

TABLE 4

Determination of the percentage and intensity of expression of CD19CAR and CD16 on CD19 t-haNK ™ clones

| | % CD16 Positive | MFI CD16 | % CD19CAR Positive | MFI CD19CAR |
|---|---|---|---|---|
| Clone #1 | 92.6 | 27.9 | 96.8 | 8.6 |
| Clone #2 | 92.7 | 19.6 | 81.5 | 2.6 |
| Clone #3 | 91.6 | 43.7 | 98.1 | 9.9 |
| Clone #4 | 94.0 | 41.0 | 94.5 | 4.3 |
| Clone #5 | 95.2 | 39.9 | 82.5 | 2.3 |
| Clone #6 | 96.8 | 30.8 | 91.9 | 2.7 |
| Clone #7 | 95.3 | 19.9 | 56.6 | 1.2 |
| Clone #8 | 88.5 | 31.1 | 95.4 | 7.7 |
| Clone #9 | 89.8 | 31.2 | 78.5 | 2.2 |
| Clone #10 | 76.1 | 44.7 | 61.8 | 1.4 |
| Clone #11 | 87.9 | 30.8 | 79.2 | 1.8 |
| Clone #12 | 99.0 | n/a | 96.3 | 4.7 |
| Clone #13 | 92.9 | 25.7 | 85.0 | 3.0 |
| Clone #14 | 93.3 | 29.9 | 82.4 | 2.7 |
| Clone #15 | 92.1 | 48.0 | 92.0 | 3.9 |
| Clone #16 | 71.0 | 28.4 | 69.2 | 2.8 |
| Clone #17 | 91.0 | 24.3 | 75.1 | 1.9 |
| Clone #18 | 90.6 | 30.0 | 81.8 | 2.7 |
| aNK | 3.1 | 1.7 | 1.6 | 0.5 |
| haNK | 94.3 | 34.0 | 23.2 | 0.7 |

The expression profile of six NK-cell markers in the selected CD19 t-haNK™ clones was determined by antibody staining and flow cytometry and compared to aNK. All clones and aNK were negative for CD3 expression, whereas only aNK was negative for CD16 expression. All clones were positive for expression of CD54, CD56, NKp30, and NKG2D, and their expression level was similar to aNK control.

TABLE 5

Determination of the percentage and intensity of expression of NK cell surface markers on CD19 t-haNK™ clones

| % MFI | CD3 | CD16 | CD54 | CD56 | NKG2D | NKP30 |
|---|---|---|---|---|---|---|
| aNK | 0.41% | 6.24% | 93.40% | 93.40% | 85.60% | 68.30% |
| | 256 | 738 | 13166 | 30520 | 2399 | 1416 |
| Clone #1 | 0.5% | 94.8% | 97.5% | 99.6% | 68.9% | 74.8% |
| | 335 | 8014 | 20729 | 34580 | 2348 | 1528 |
| Clone #4 | 0.6% | 94.3% | 99.3% | 99.3% | 97.4% | 82.6% |
| | 263 | 9275 | 8861 | 46751 | 2079 | 1420 |
| Clone #5 | 0.3% | 94.0% | 97.9% | 96.9% | 82.3% | 67.1% |
| | 349 | 8211 | 10769 | 36529 | 2143 | 1721 |
| Clone #6 | 0.8% | 96.0% | 97.2% | 97.4% | 95.7% | 68.7% |
| | 330 | 8727 | 14514 | 35217 | 4318 | 2209 |
| Clone #9 | 6.9% | 93.4% | 97.9% | 96.7% | 77.3% | 82.1% |
| | 922 | 8186 | 12053 | 36752 | 2526 | 1880 |
| Clone #11 | 8.8% | 91.5% | 93.4% | 90.6% | 91.7% | 76.4% |
| | 1277 | 9163 | 13368 | 34580 | 4138 | 2183 |
| Clone #12 | 2.5% | 89.4% | 96.2% | 90.9% | 72.4% | 95.5% |
| | 453 | 6574 | 11272 | 25191 | 2433 | 5680 |
| Clone #14 | 0.9% | 89.4% | 97.3% | 93.6% | 66.3% | 95.7% |
| | 359 | 7426 | 13532 | 32536 | 1966 | 5344 |
| Clone #15 | 1.1% | 90.5% | 96.8% | 96.2% | 93.9% | 69.8% |
| | 347 | 14736 | 13993 | 36752 | 4983 | 2399 |
| Clone #18 | 2.2% | 98.0% | 97.8% | n/a | 99.1% | 95.6% |
| | 316 | 6987 | 11692 | | 4189 | 1538 |

Example 4: Cytotoxicity of CD19 t-haNK™ Cells on Target Cell Lines

Figure 4B:
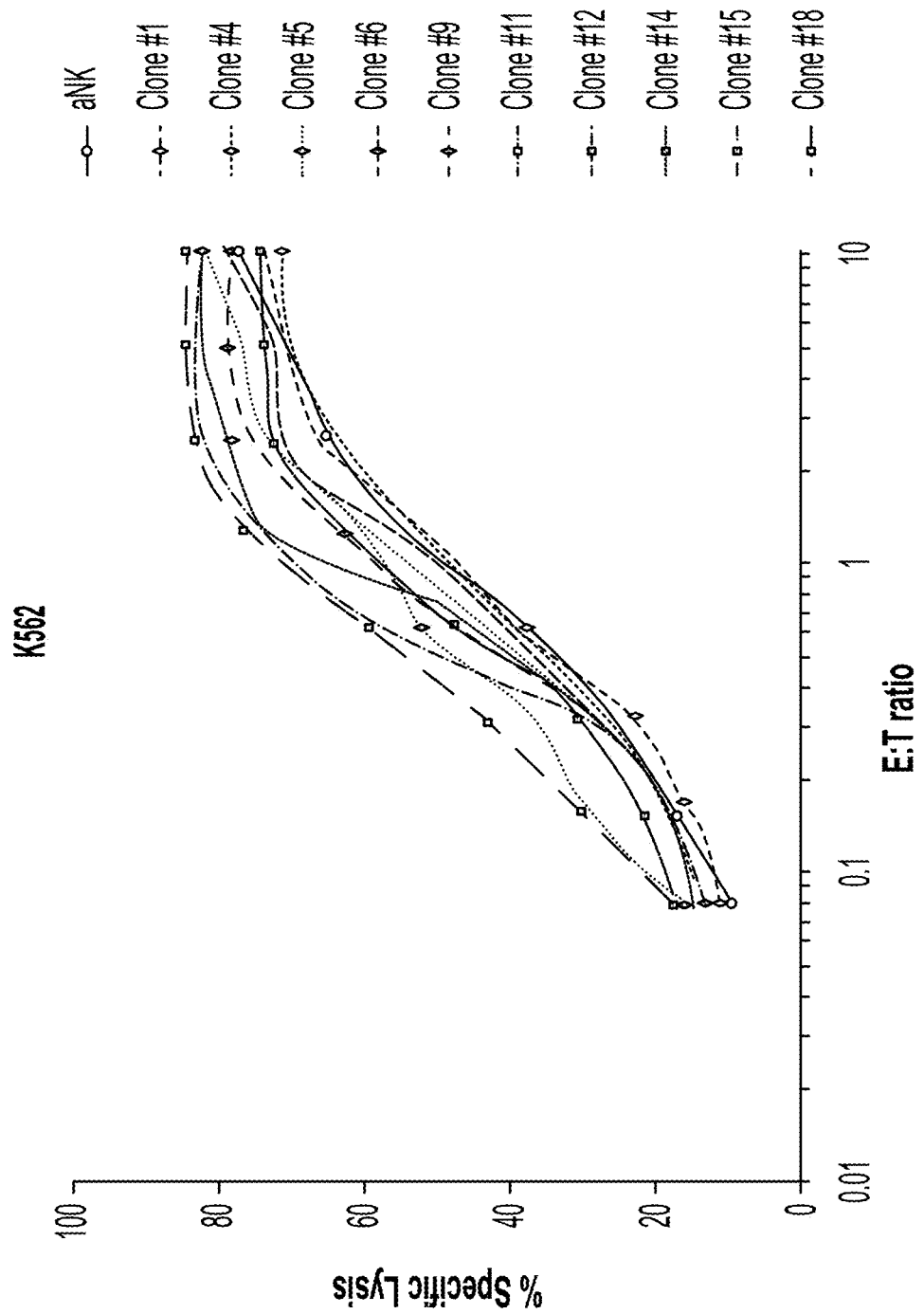
FIG. 4B shows cytotoxic effect of selected CD19 t-haNK™ clones on K562 in a cytotoxicity assay.

The cytotoxicity of CD19 t-haNK™ cells were analyzed by incubating with target cells K562 cells, SUP-B15 cells, and SKBr cells. FIG. 4A shows that CD19 t-haNK™ cells maintained comparable cytotoxicity to parental aNK cells in killing K562 cells (target cells). 16B1 and 18B1 are two CD19 t-haNK™ populations obtained from two electroporation events conducted on different days.

In a separate experiment, selected CD19 t-haNK™ clones were used as effectors in flow cytometry-based in vitro cytotoxicity assays against the K562 target cell line (CD19−, NK-sensitive). All clones displayed efficient cytolytic activity against K562 in a 4 h cytotoxicity assay. The average maximum killing efficiency for the CD19 t-haNK™ clones was between 70.9±10.1% and 84.4±0.6% at a 10:1 ratio, compared to 84.1±2.4% for aNK control (n=2 to 5). See FIG. 4B.

Figure 5A:
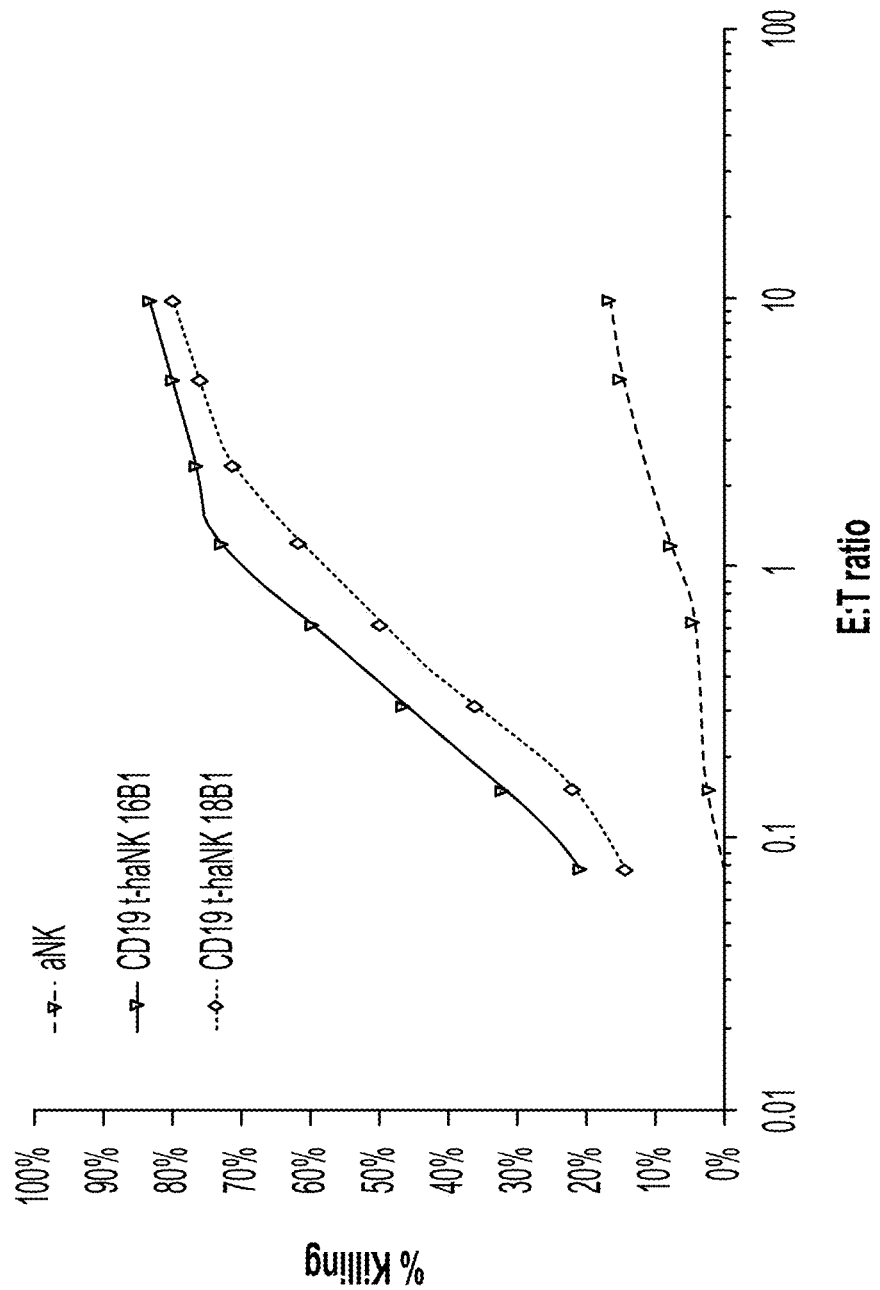
FIG. 5A shows the cytotoxic effect of CD19 t-haNK™ cells on SUP-B15 cells. 16B1 and 18B1 are two CD19 t-haNK™ populations obtained from two electroporation events performed on two different days.

FIG. 5A shows that CD19 t-haNK™ cells demonstrated enhanced specific killing of the aNK™-resistant, CD19-positive SUP-B15 cell line—about 80-90% of cells were killed by CD19 t-haNK™ cells relative to only about 10-20% of cells were killed by aNK cells at an effector to target ratio of 10.

Figure 5B:
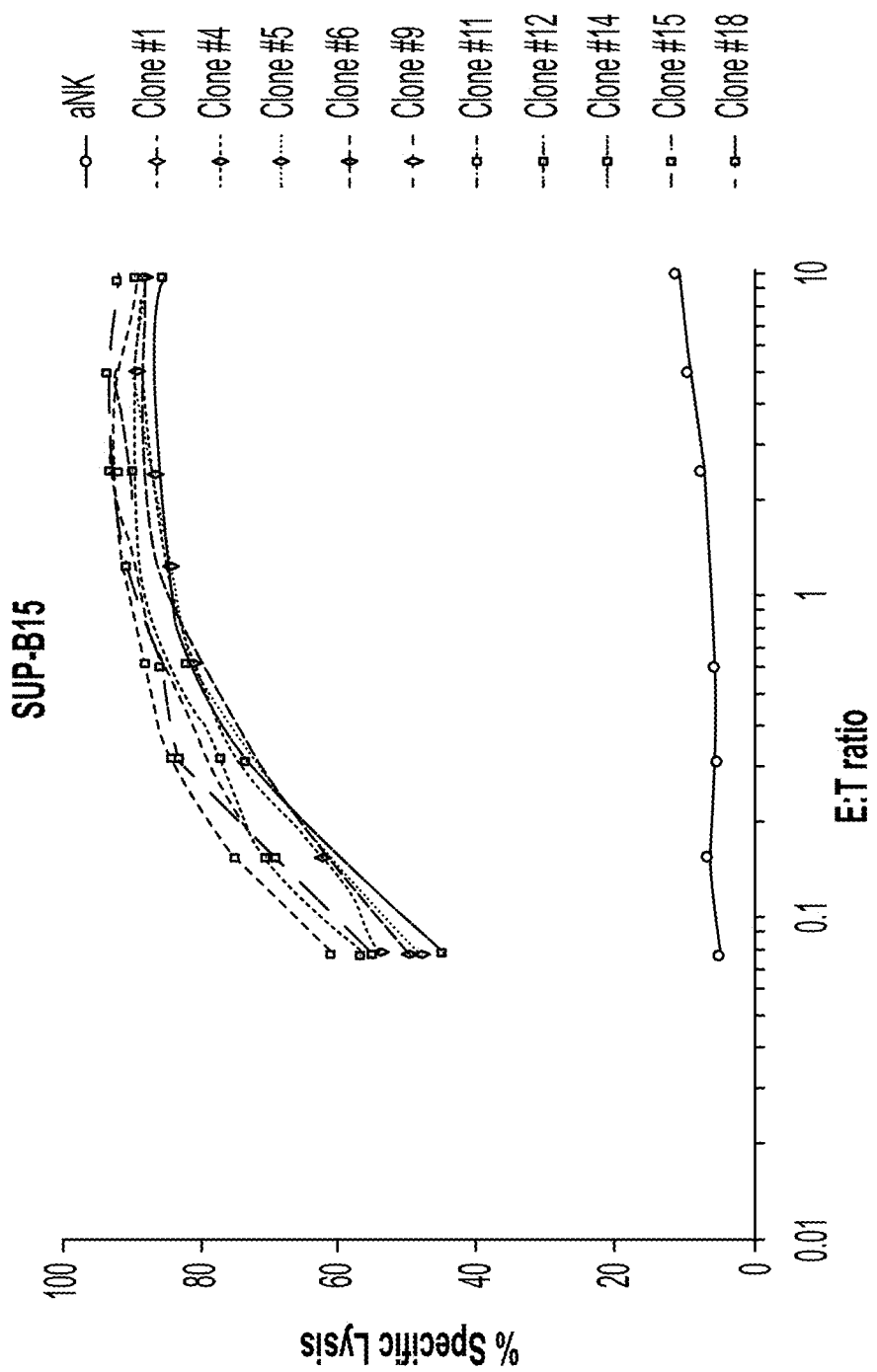
FIG. 5B shows cytotoxic effect of selected CD19 t-haNK™ clones on SUP-B15 in a cytotoxicity assay.

In a separate experiment, Selected CD19 t-haNK™ clones were used as effectors in flow cytometry-based in vitro cytotoxicity assays against the SUP-B15 target cell line (CD19+, NK-resistant). All clones were able to efficiently target and kill the resistant SUP-B15 in a 4 h cytotoxicity assay. The average maximum killing efficiency for the CD19 t-haNK™ clones was between 85.7±0.1% and 92.2±1.2% at a 10:1 ratio, compared to 10.8±7.4% for aNK control (n=2 to 5). See FIG. 5B.

Figure 6B:
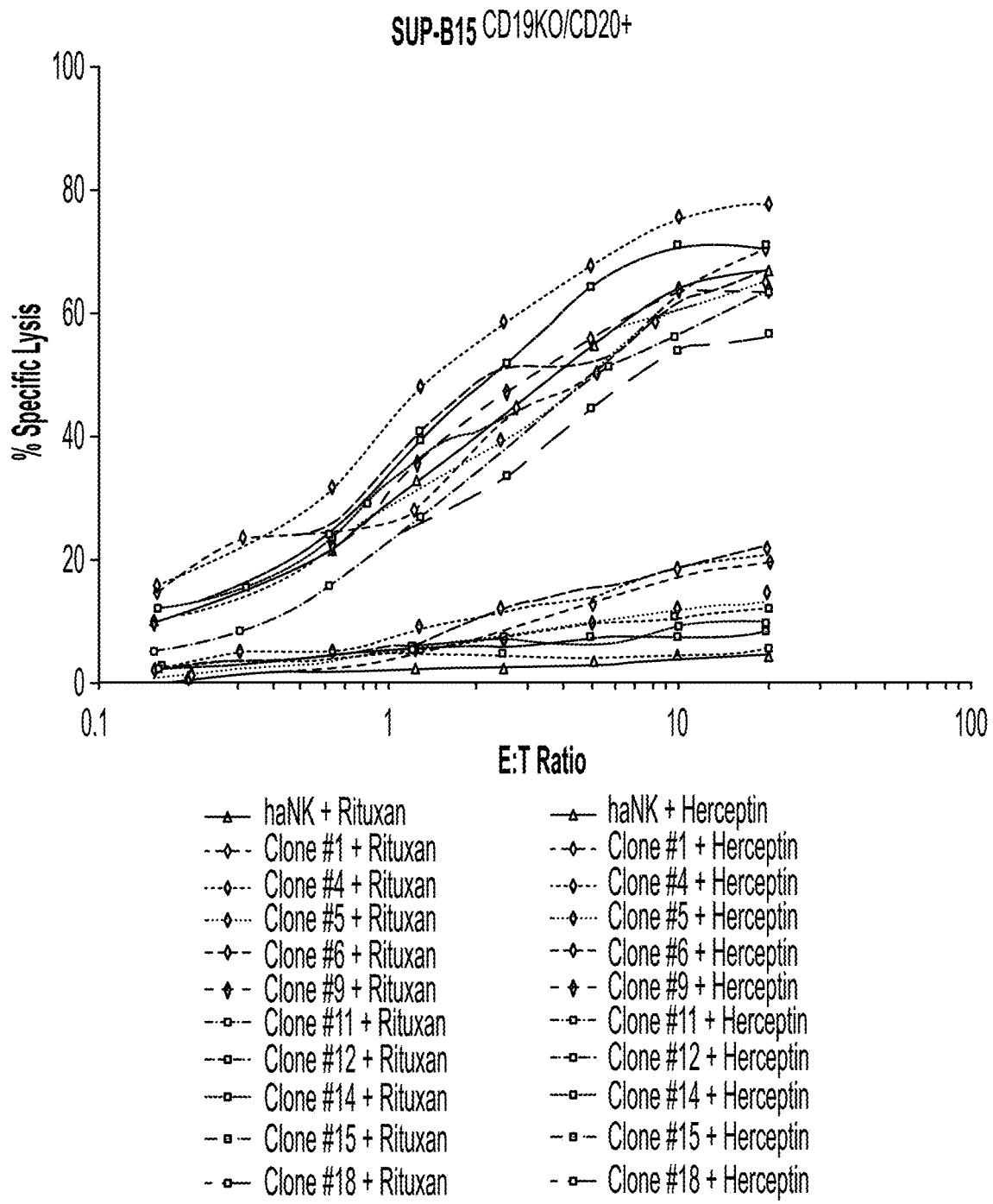
FIG. 6B shows the ADCC activity of the selected CD19 t-haNK™ clones on SUP-B15 cells that are CD19KO/CD20+ when combined with the anti-CD20 antibody rituximab.

FIG. 6A shows that the ADCC activity of the CD19 t-haNK™ cells on SKBr3 cells (CD19−, Her2/neu+) was comparable to that of haNK® cells expressing the CD16 (158V) receptor only, when combined with the anti-Her2/neu antibody Herceptin.

In another experiment, selected CD19 t-haNK™ clones were used as effectors in flow cytometry-based in vitro ADCC assays against a modified SUP-B15 target cell line (CD19−, CD20+, Her2−neu−, NK-resistant) in combination with anti-CD20 rituximab monoclonal antibody or with anti-Her2-neu trastuzumab monoclonal antibody. In a 4 h cytotoxicity assay, all clones were able to efficiently target and kill the resistant SUP-B15CD19KO/CD20+ when combined with the anti-CD20 antibody rituximab. The maximum killing efficiency for the CD19 t-haNK™ clones was between 63.7% and 77.8% at a 10:1 ratio, compared to 67.1% for haNK® control (n=1 to 2). Neither haNK® nor the CD19 t-haNK™ clones were able to kill target SUP-B15CD19KO/CD20+ cells when combined with the anti-Her2/neu control antibody trastuzumab (maximum killing efficiency for the CD19 t-haNK™ clones between 7.7% and 21.9% at a 10:1 ratio, and 4.1% for haNK®). ADCC-mediated killing for the CD19 t-haNK™ clones was between 46.4% and 65.2% at a 10:1 ratio, compared to 62.7% for haNK® control. See FIG. 6B.

Example 5: Other Properties of CD19 t-haNK™ Cells

Figure 7:
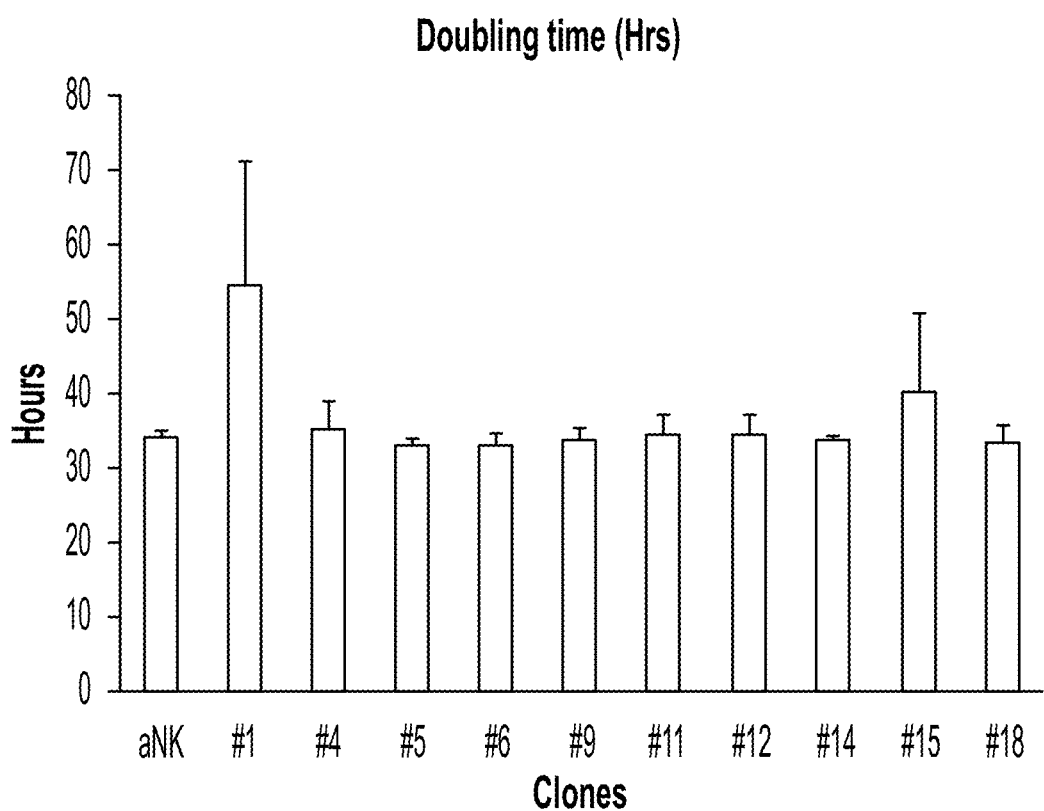
FIG. 7 shows that doubling time of the selected CD19 t-haNK™ clones.

The population doubling time of selected CD19 t-haNK™ clones was determined by a cell growth assay over 7 days without medium change, and average doubling times were calculated. All clones had a population doubling time ranging from 33.1 to 54.5 hrs, compared to 34.5 hrs for the aNK control. See FIG. 7.

Figure 8:
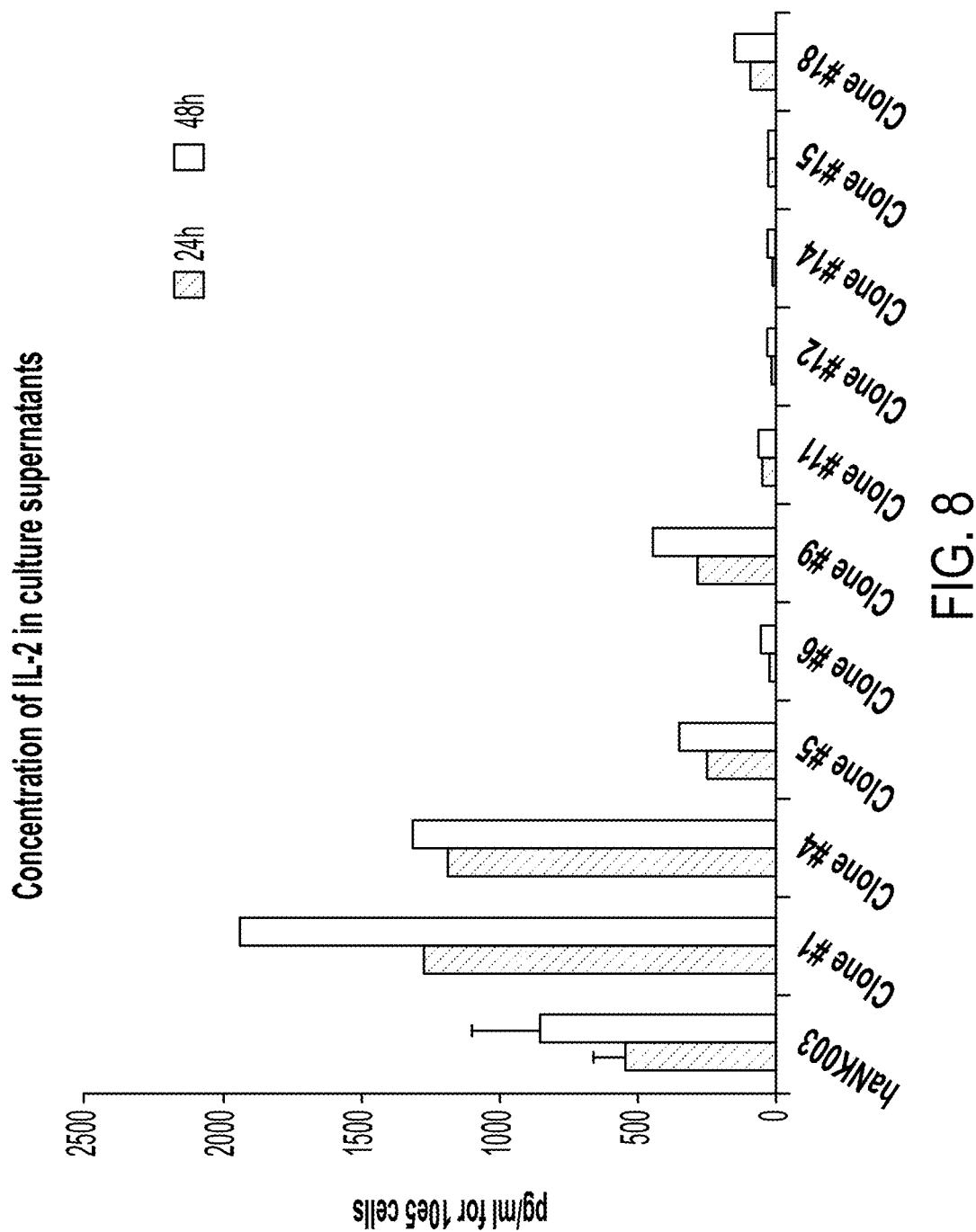
FIG. 8 shows that IL-2 release from the selected CD19 t-haNK™ clones in culture conditions.

CD19 t-haNK™ clones were put in culture in 6-well plates at a density of 10e5 cells/ml without IL-2, and culture supernatants were harvested after 24 and 48 h. The supernatants were analyzed by ELISA to detect and measure potential release of ERIL-2 by the CD19 t-haNK™ cells. At 24 h in culture, CD19 t-haNK™ clones released between 16.1 and 1278.5 pg/ml/105 cells. See FIG. 8.

Example 6: CD19 t-haNK™: Evaluation of Anti-Tumor Activity of CD19-Targeting t-haNK™ Cells in Intravenous and Subcutaneous Models of Raji Human Burkitt's Lymphoma in NSG Mice CD19 t-haNK™s are Natural Killer cells that express a chimeric antigen receptor (CAR) against CD19 to treat hematological cancers of the B-cell lineage. In the present study, the anti-tumor effects of repeated intravenous (IV) administrations of CD19 t-haNK™s were evaluated in both IV and subcutaneous (SC) Raji xenograft models in NSG mice. In both models, CD19 t-haNK™ cells demonstrated significant therapeutic efficacy. Specifically, in the IV tumor model, CD19 t-haNK™ cells significantly improved animal survival as compared to the vehicle control. In the SC tumor model, CD19 t-haNK™ was able to significantly suppress tumor growth, reduce the number of animal morbidity/death events, and markedly decrease metastatic disease burden in the liver.

It has previously been shown that targeted aNK cells that express a chimeric antigen receptor (CAR) against CD19 exhibited efficacy in Raji tumor-bearing NSG mice, most likely due to target-specific cytotoxicity in the CAR-expressing cells (See, for example, Oelsner et al, Cytotherapy, 2017). In this study, the efficacy of CD19 t-haNK™ cells were evaluated in two different variations of the Raji xenograft model: 1) intravenously (IV) inoculated Raji cells; and 2) subcutaneously (SC) inoculated Raji tumors, with both models receiving repeated IV doses of CD19 t-haNK™ cells. Note that additional groups of animals (groups B and E) were also included in the original study protocol to be evaluated in this model, but are not being included in this report since they were not relevant to the CD19 t-haNK™ efficacy determination (see Table 6 for the abbreviated experimental design).

Example 7: Materials for the CD19 t-haNK™ Study

CD19 t-haNK™ cells (clone 19.6): CD19 t-haNK™ cells were cultured in growth medium supplemented with 5% heat inactivated human AB serum by following the protocol provided by Process Development, NantKwest®, Inc., Torrey Pines.

Test Animals: The test animals used were female NOD.Cg-Prkdc$^{scid}$Il2rg$^{tm1Wjl}$/SzJ (NSG) mice of age between 9-10 weeks at study initiation (after quarantine) and having body weight between 20-27 grams at study initiation. 20 animals were for the IV tumor model, while 12 were for the SC tumor model. The supplier of the animals was The Jackson Laboratory (610 Main Street Bar Harbor, ME 04609 US). A sterile stainless steel ear tag was applied to each mouse with a hand-held applicator for identification. In addition, each cage had a cage card that contained study number and animal number information.

Raji Cancer Cell Line: Raji cells were originally purchased from ATCC (Catalog # CCL-86™; Lot #61723871) and then expanded and prepared by Preclinical Development, NantKwest®, Inc. The cells were authenticated by IDEXX on Mar. 18, 2018 (see Appendix 2 for authentication report). Cell Culture Medium was ATCC-formulated RPMI-1640 medium supplemented with 10% fetal bovine serum with penicillin (100 U/mL), streptomycin (100 µg/mL). Raji cells (passage 12) in exponential phase were collected by centrifugation. Cells were washed and re-suspended in serum free medium at the concentration of $5\times10^5$ viable cells/mL for IV inoculations, and in medium/Matrigel (1:1 v/v) at the concentration of $2.5\times10^6$ viable cells/mL for SC implantations. Cells were stored on ice prior to animal injection. Cells used in the in vivo study had a viability of 96%.

Raji IV Model: 20 animals were injected IV via the lateral tail vein with 0.2 mL of Raji cell suspension with 27-gauge needles ($1\times10^5$ cells inocula).

Raji SC Model: 12 animals were implanted SC on both flanks with 0.1 mL of Raji cell suspension with 25-gauge needles ($2.5\times10^5$ cells inocula).

Example 8: Experimental Procedures for the CD19 t-haNK™ Study

IV Raji Model: Within 24 hours after cancer cell inoculation, which was defined as Day 1, 20 animals were pseudo-randomized into 2 groups of 10 according to body weight to achieve similar average body weight between the groups. On Days 2, 5, 8, 10, 12, and 17, CD19 t-haNK™ cells grown in the exponential phase were harvested by centrifugation and formulated in growth medium at the concentration of $5\times10^7$ cells/mL for IV administration at the dose of $1\times10^7$ cells per mouse with an injection volume of 200 µL. As shown in Table 6, animals in Group A received the vehicle control, while animals in Group C received CD19 t-haNK™ cells.

Animals were weighed prior to tumor cell injection and twice weekly. Animals were observed daily for mortality/morbidity (G0 to G4) and clinical signs of toxicity (T1 to T12; see Table 6). Paralyzed or moribund animals were euthanized. Animals were euthanized with $CO_2$ inhalation followed by cervical dislocation. Mortality events (euthanasia or spontaneous) were recorded in Death Log and tallied to calculate the survival curve.

SC Raji Model: After SC tumor implantation, animals were examined at least twice a week for tumor establishment. When tumors became palpable, tumor volumes (TV) were measured with a digital hand held caliper once to twice weekly, and calculated using this formula: TV=Length× Width$^2$/2 [Length being the greatest diameter and Width being the shortest diameter of the tumor]. When the average tumor volume reached an injectable size (195 mm$^3$ in this case; 24 days post-implantation), the 12 tumor-bearing animals were pseudo-randomized into 2 groups of 6 to achieve similar tumor volumes between the groups. This was defined as Day 0. On Days 1, 4, 7, 9, 11, and 13, CD19 t-haNK™ cells grown in the exponential phase were harvested by centrifugation, subjected to 1000 cGy gamma irradiation, and formulated in growth medium at the concentration of $5\times10^7$ cells/mL for IV administration at the dose of $1\times10^7$ cells per mouse with an injection volume of 200 µL. As shown in Table 6, animals in Group D received the vehicle solution, while animals in Group F received CD19 t-haNK™ cells. Animals were weighed prior to tumor cell injection and then twice weekly.

Animals were observed daily for mortality/morbidity (G0 to G4) and clinical signs of toxicity (T1 to T12). Paralyzed or moribund animals were euthanized. While moribund animals were euthanized as soon as they showed morbidity, surviving animals were subjected to scheduled euthanasia for tissue collection. Specifically, half of the surviving animals (up to 3 mice/group) were euthanized on Day 13 at 6 hours post the last dose of test article administration. The rest of the animals were euthanized on Day 15 at 48 hours post the last dosing. Euthanasia was performed by cervical dislocation while animals were under deep anesthesia following a terminal intra-cardiac bleeding. The blood/serum samples were not analyzed in this portion of the study and therefore not included in this report.

Upon termination, a necropsy was performed and organs with visible gross lesions were collected, fixed in 10% formalin, and submitted to a contract pathology laboratory (Seventh Wave Laboratories) for histological evaluation of tumor/metastatic disease burden.

TABLE 6

Study Design (abbreviated)

| Group | N | Tumor Model | Treatment | Tx Route | NK Cell Dose | Treatment Days | Endpoint |
|---|---|---|---|---|---|---|---|
| A | 10 | IV | Vehicle | IV | / | 2, 5, 8, 10, 12, and 17 | Moribund |
| C | 10 | IV | CD19 t-haNK ™, non-IR | IV | $1 \times 10^7$ | 2, 5, 8, 10, 12, and 17 | Moribund |
| D | 6 | SC, bilateral | Vehicle | IV | / | 1, 4, 7, 9, 11, and 13 | Days 13 and 15 or Moribund |
| F | 6 | SC, bilateral | CD19 t-haNK ™, IR | IV | $1 \times 10^7$ | 1, 4, 7, 9, 11, and 13 | Days 13 and 15 or Moribund |

IR, irradiated (1000 cGy); non-IR, non-irradiated; IV, intravenous; SC, subcutaneous; Tx, treatment.

Example 9: Data Analysis for the CD19 t-haNK™ Study

Tumor volume was calculated using the following equation: Tumor volume=Length×Width/2 (Length and Width being the longest and shortest diameters of the tumor, respectively).

Tumor Growth Inhibition (TGI) Calculation was done was follows: TGI=$(T_C-T_t)/\Delta T_C \times 100\%$, where $T_C$ and $T_t$ is the average tumor volume for control and treatment groups at the end of the study, respectively, and $\Delta T_C$ is the change in average tumor volume in the control group.

Tumor growth curves were analyzed by 2-way ANOVA followed by multiple comparisons by Tukey test. Survival curves were analyzed by Log-rank (Mantel-Cox) test. Differences in liver metastatic disease burden on individual days were analyzed by unpaired 2-tailed t test. P<0.05 is considered statistically significant. All statistical analyses were performed using GraphPad Prism version 7.

Example 10: IV Raji Model Results for the CD19 t-haNK™ Study

Figure 9:
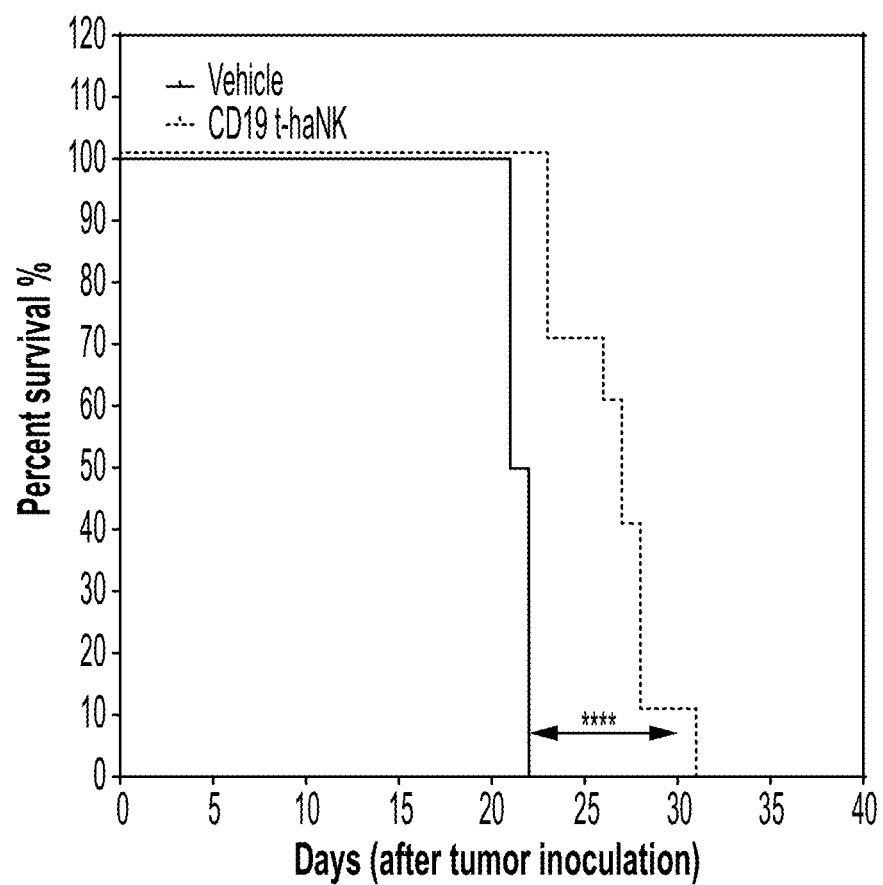
FIG. 9 shows Survival curve of IV Raji tumor bearing animals. Statistical analysis was done by Log-rank (Mantel-Cox) test. ****, P<0.0001.
Figure 10:
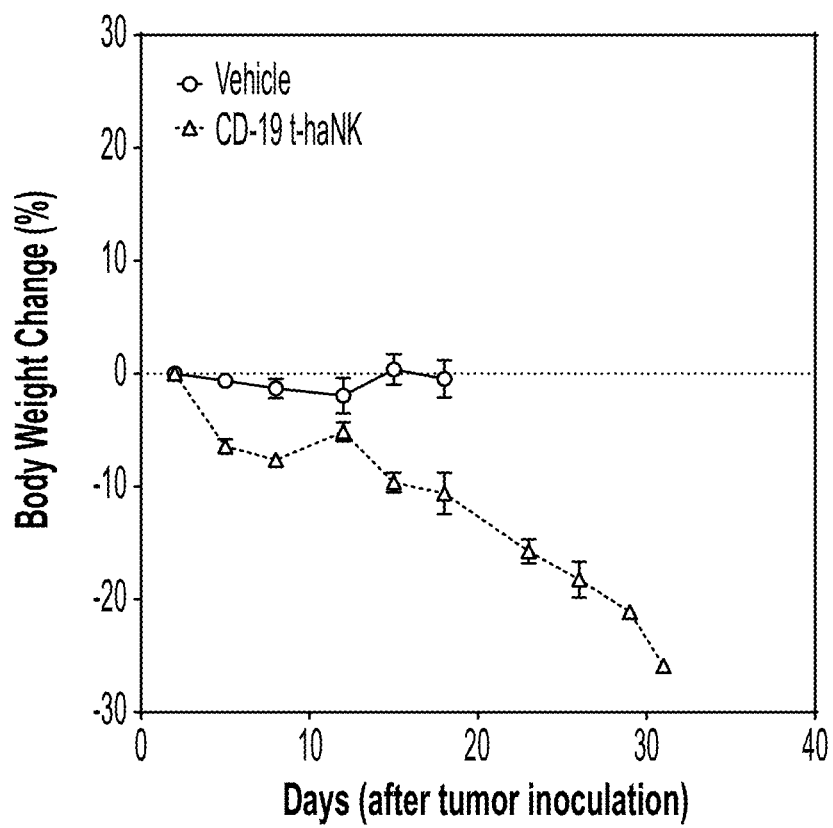
FIG. 10 shows animal body weight change in the IV Raji tumor model. Data are mean±SEM. SEM was calculated as Standard Deviation divided by the square root of N.

The main readout in the IV tumor model was animal survival. A death event was counted when an animal was found dead or was euthanized due to disease-related morbidity and/or paralysis. As shown in FIG. 9, compared to vehicle control, CD19 t-haNK™ cell treatment was able to significantly improve the animals' rate of survival, resulting in a median survival of 27 days versus 21.5 days in the vehicle control group (P<0.0001). Animal body weight change was also monitored throughout the study. As shown in FIG. 10, CD19 t-haNK™ treated animals demonstrated a moderate (less than 10%) and short-term body weight loss when treatment was first initiated, which is not an uncommon phenomenon in animals receiving IV NK infusions, and not specific to the CD19 t-haNK™ cells. Their body weight was able to recover after the first week of treatment before decreasing again due to disease progression.

Example 11: SC Raji Model Results for the CD19 t-haNK™ Study

Figure 11:
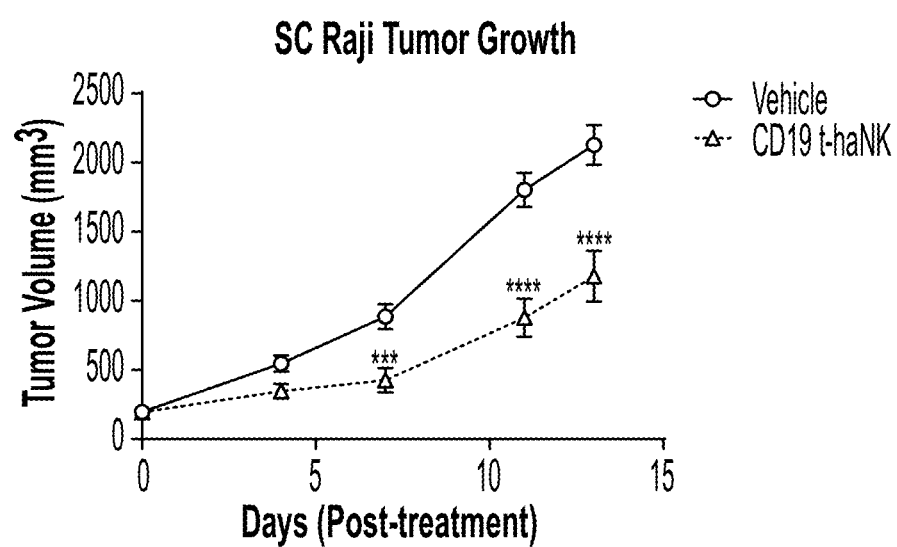
FIG. 11 shows tumor growth curve for the SC Raji model. Data are Mean±SEM. Statistical analyses were done using 2-way ANOVA followed by multiple comparison by Tukey test; *, P<0.001; **, P<0.0001.

The primary readout in the SC tumor model was tumor growth. As shown in FIG. 11, CD19 t-haNK™ cells demonstrated evident and statistically significant tumor growth inhibition on and after Day 7 compared to the vehicle control group, with a 49% TGI at the end of the study (Day 13).

Further, as Raji is an aggressive lymphoma model, even when inoculated SC, the cancer cells were able to dissemi-nate and develop multiple sites of metastases that eventually led to animal morbidity and/or death. There were a total of 3 animals (50%) that were moribund between Days 11 and 13 and therefore were euthanized in the vehicle group. In contrast, there was no unscheduled death event in the CD19 t-haNK™ cells group (Table 7).

Figure 12:
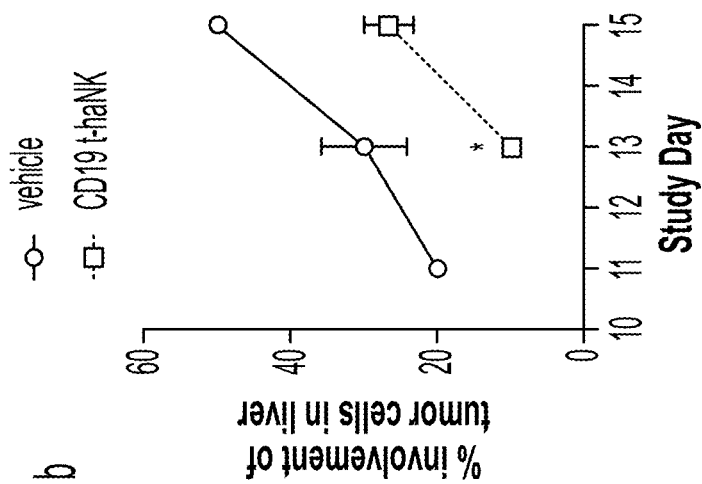
FIG. 12 shows CD19 t-haNK™ reduced metastatic disease burden in the livers of SC Raji tumor-bearing mice. (a) Whole liver images of animals from indicated treatment groups on Day 13. Yellow arrows indicate metastatic lesions. Livers were fixed in 10% formalin for at least 24 hours prior to photography. (b) Quantification of percentage involvement of tumor cells in the liver (evaluated by H&E staining) on indicated days. On Day 13: *, P=0.0257 by unpaired 2-tailed t test. Statistical analyses for Days 11 and 15 could not be performed due to limited sample size. See Table 4 for raw data.
Figure 13:
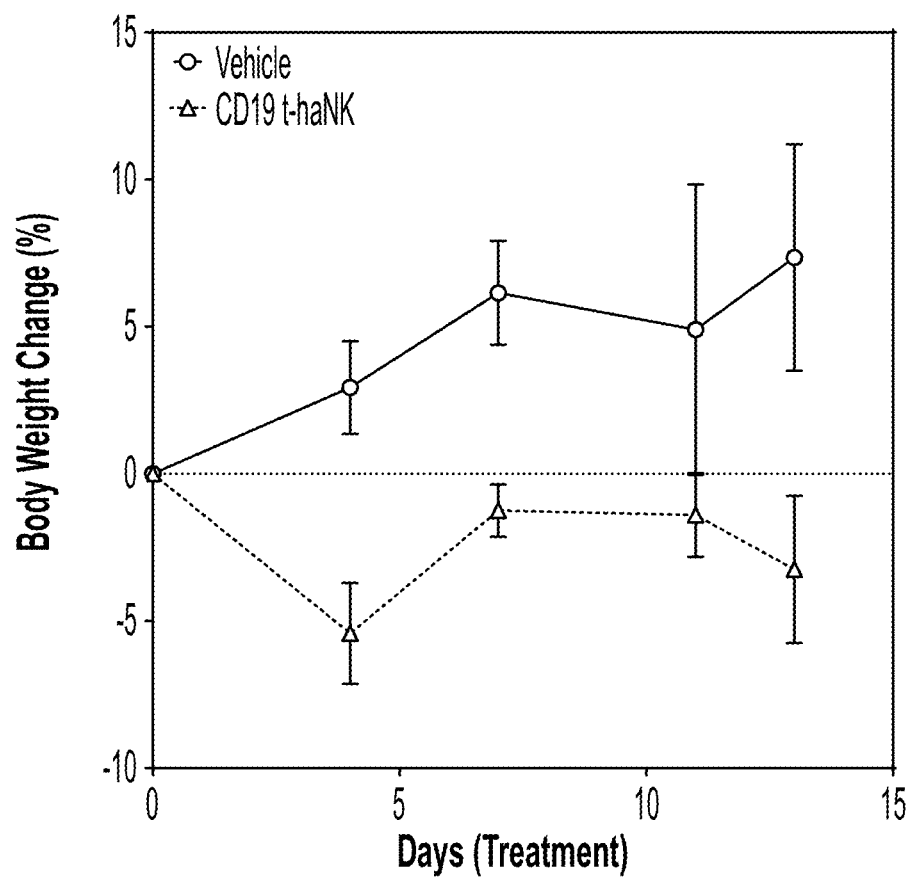
FIG. 13 shows animal body weight change in the SC Raji tumor model. Data are mean±SEM.

In addition, a qualitative reduction of liver metastases was observed in CD19 t-haNK™ treated animals during necropsy (FIG. 12a). A semi-quantitative estimation of the disease burden was performed by a contract pathology lab (Seventh Wave Laboratories) on H&E stained liver sections that were representatively sampled. As summarized in FIG. 12b and Table 8, there was a clear trend of increasing disease burden as the study advanced. Livers of CD19 t-haNK™ treated animals exhibited a remarkably lower percentage of cancer infiltrated areas compared to the vehicle control. Due to the small sample number and unscheduled early mortality in the control group, statistical analysis could only be performed on the Day 13 data. This analysis showed a significant difference in disease burden, with an average of 10% infiltration in CD19 t-haNK™ treated animals versus 30% in the control group. Body weight change was monitored throughout the study, and similar to the IV Raji model, CD19 t-haNK™ treated animals demonstrated a moderate (less than 10%) and transient body weight loss in the beginning of the treatment regimen (FIG. 13).

TABLE 7

Mortality/Death Log for Animals in the SC Raji Model

| Group | Initial N | Day 11 | Day 13 | Day 15 |
|---|---|---|---|---|
| D (Vehicle) | 6 | 2 × Moribund | 1 × Moribund | |
| | | | 2 × Scheduled | 1 × Scheduled |
| F (CD19 t-haNK ™) | 6 | | | |
| | | | 3 × Scheduled | 3 × Scheduled |

Scheduled: scheduled euthanasia for tissue collection.

TABLE 8

Percent Involvement of Tumor Cells in Liver

| Group (Treatment) | Animal Number | Collection Day | Estimated % Tumor | Mean |
|---|---|---|---|---|
| D (Vehicle) | 503 | 11 | 20 | 20 |
| | 520 | 11 | 20 | |
| | 487 | 13 | 40 | 30 |
| | 488 | 13 | 20 | |
| | 497 | 13 | 30 | |
| | 502 | 15 | 50 | 50 |

TABLE 8-continued

Percent Involvement of Tumor Cells in Liver

| Group (Treatment) | Animal Number | Collection Day | Estimated % Tumor | Mean |
|---|---|---|---|---|
| F (CD19 t-haNK™) | 495 | 13 | 10 | 10 |
| | 505 | 13 | 10 | |
| | 507 | 13 | 10 | |
| | 512 | 15 | 30 | 27 |
| | 522 | 15 | 30 | |
| | 525 | 15 | 20 | |

Example 12: Conclusions of the CD19 t-haNK™ Study

To assess the anti-tumor efficacy of CD19 t-haNK™ cells in repeated IV dosing regimens, 2 variations of the Raji xenograft model with IV and SC tumor inoculations, respectively, were utilized in this study. In the IV tumor model, CD19 t-haNK™ cells were able to significantly improve animal survival, prolonging median survival by 5.5 days (a 26% increase) compared to the vehicle control group. In the SC tumor model, CD19 t-haNK™ cells were able to significantly suppress tumor growth, resulting in a 49% TGI at the end of the study. Furthermore, CD19 t-haNK™ treatment was able to reduce the number of animal morbidity/death event (0/6 in CD19 t-haNK™ treated animals versus 3/6 in the control group), and markedly decrease metastatic disease burden in the liver of SC Raji-tumor bearing animals. Overall, CD19 t-haNK™ cells displayed significant therapeutic efficacy compared to vehicle control in both variations of the Raji xenograft model.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A recombinant nucleic acid comprising a sequence that encodes an anti-cluster of differentiation 19 (CD19) chimeric antigen receptor (CAR), wherein the anti-CD19 CAR comprises an antigen binding domain comprising a CD19-specific single chain variable fragment (scfv), wherein the C-terminus of the scfv is fused via a peptide linker to the N-terminus of a hinge domain, wherein an intracellular signaling domain comprises the hinge domain at its N-terminus, a transmembrane domain, and an Fc∈RIγ cytoplasmic signaling domain at its C-terminus, and wherein the intracellular signaling domain has the amino acid sequence of amino acids 274-407 of SEQ ID NO: 12.

2. The recombinant nucleic acid of claim 1 further comprising a nucleic acid sequence that encodes a fragment crystallizable receptor RIII (FcγRIIIA).

3. The recombinant nucleic acid of claim 2 wherein the FcγRIIIA receptor has the amino acid sequence of SEQ ID NO: 1.

4. The recombinant nucleic acid of claim 2 wherein the FcγRIIIA receptor has the amino acid sequence of SEQ ID NO:2.

5. The recombinant nucleic acid of claim 1 further comprising a nucleic acid sequence that encodes a cytokine.

6. The recombinant nucleic acid of claim 5 wherein the cytokine is interleukin 2 (IL-2) or interleukin 15 (IL-15).

7. The recombinant nucleic acid of claim 6 wherein the cytokine has the amino acid sequence of SEQ ID NO:6 (IL2).

8. The recombinant nucleic acid of claim 2 further comprising a nucleic acid sequence that encodes a cytokine.

9. The recombinant nucleic acid of claim 8 wherein the FcγRIIIA receptor has the amino acid sequence of SEQ ID NO: 1 or SEQ ID NO:2, and wherein the cytokine has the amino acid sequence of SEQ ID NO:6 or SEQ ID NO:7.

10. The recombinant nucleic acid of claim 8 wherein the nucleic acid sequence that encodes the anti-CD19 CAR, the nucleic acid sequence that encodes the FcγRIIIA receptor, and the nucleic acid sequence that encodes the cytokine are arranged in a tricistronic construct.

11. The recombinant nucleic acid of claim 10 further comprising a nucleic acid sequence that encodes a P2A peptide, wherein the nucleic acid sequence that encodes a P2A peptide is between the nucleic acid sequence that encodes the anti-CD19 CAR and the nucleic acid sequence that encodes the Fc receptor, and further comprising a nucleic acid sequence comprising an internal ribosome entry site (IRES), wherein the sequence comprising an IRES is between the nucleic acid sequence that encodes the Fc receptor and the nucleic acid sequence that encodes the cytokine.

12. The recombinant nucleic acid of claim 10 wherein the tricistronic construct encodes a protein sequence having the amino acid sequence of SEQ ID NO: 14.

13. A recombinant vector comprising the recombinant nucleic acid of claim 1.

14. The recombinant vector of claim 13 having the nucleic acid sequence of SEQ ID NO: 13 or a portion thereof, wherein the portion comprises the recombinant nucleic acid of claim 1.

15. The recombinant nucleic acid of claim 6, wherein the IL-2 or IL-15 further comprises an endoplasmic reticulum retention sequence.

16. The recombinant nucleic acid of claim 15, wherein the cytokine has the amino acid sequence of SEQ ID NO:7 (er-IL2).

17. A recombinant NK cell comprising the nucleic acid of claim 1.

18. The recombinant NK cell of claim 17, wherein the NK cell is an NK-92 cell.

19. The recombinant nucleic acid of claim 1, wherein the peptide linker is comprised of at least 2 alanine residues.

* * * * *